US009186219B2

(12) United States Patent
Stefanchik et al.

(10) Patent No.: US 9,186,219 B2
(45) Date of Patent: Nov. 17, 2015

(54) SURGICAL SYSTEM AND METHODS FOR MIMICKED MOTION

(75) Inventors: David Stefanchik, Morrow, OH (US);
Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 619 days.

(21) Appl. No.: 12/971,434

(22) Filed: Dec. 17, 2010

(65) Prior Publication Data

US 2012/0158013 A1    Jun. 21, 2012

(51) Int. Cl.
*A61B 19/00* (2006.01)
*A61B 17/29* (2006.01)
*A61B 17/34* (2006.01)
*A61B 17/00* (2006.01)

(52) U.S. Cl.
CPC .................. *A61B 19/22* (2013.01); *A61B 17/29* (2013.01); *A61B 17/3417* (2013.01); *A61B 2017/00477* (2013.01); *A61B 2019/2223* (2013.01); *A61B 2019/2242* (2013.01); *A61B 2019/2269* (2013.01); *A61B 2019/265* (2013.01)

(58) Field of Classification Search
CPC ....................................................... A61B 19/22
USPC ........... 248/127, 181; 606/1, 130; 414/7, 1, 2, 414/4; 33/25.1; 475/202
See application file for complete search history.

(56) References Cited

U.S. PATENT DOCUMENTS

| | | | | |
|---|---|---|---|---|
| 3,212,651 A | * | 10/1965 | Specht et al. | 414/7 |
| 3,282,442 A | * | 11/1966 | Culshaw et al. | 414/7 |
| 3,664,517 A | * | 5/1972 | Germond et al. | 414/7 |
| 4,221,516 A | * | 9/1980 | Haaker et al. | 414/5 |
| 4,549,839 A | * | 10/1985 | Glachet et al. | 414/7 |
| 4,756,655 A | * | 7/1988 | Jameson | 414/2 |

(Continued)

FOREIGN PATENT DOCUMENTS

| | | |
|---|---|---|
| FR | 2845889 A1 | 4/2004 |
| WO | 03/086219 A2 | 10/2003 |

(Continued)

OTHER PUBLICATIONS

FlexDex: A Minimally Invasive Surgical Tool with Enhanced Dexterity and Intuitive Control, Awtar et al., Journal of Medical Devices, Sep. 2010, vol. 4.

(Continued)

*Primary Examiner* — Richard Louis
(74) *Attorney, Agent, or Firm* — Nutter McClennen & Fish LLP

(57) ABSTRACT

The present invention generally provides methods and devices for controlling movement of an end effector, and in particular for causing mimicked motion between an input tool and an end effector during a surgical procedure. In an exemplary embodiment, a surgical system is provided having a master assembly with an input tool and a slave assembly with an end effector. The master assembly and the slave assembly can be coupled together by a mechanical assembly that is configured to mechanically transfer mimicked, rather than mirrored, motion from the input tool to the end effector. A floating frame is also provided and can be utilized with the surgical system. The floating frame can have a counterbalance that allows the surgical system to "float" above a patient and provide a weightless feel to movement of the surgical system. The floating frame can provides additional degrees of freedom for movement of the surgical system.

11 Claims, 25 Drawing Sheets

(56) References Cited

U.S. PATENT DOCUMENTS

| | | | |
|---|---|---|---|
| 4,762,455 A | | 8/1988 | Coughlan et al. |
| 5,330,502 A | | 7/1994 | Hassler et al. |
| 5,697,939 A | | 12/1997 | Kubota et al. |
| 5,702,408 A | | 12/1997 | Wales et al. |
| 5,716,352 A | | 2/1998 | Viola et al. |
| 5,784,542 A | | 7/1998 | Ohm et al. |
| 5,792,135 A | | 8/1998 | Madhani et al. |
| 5,951,574 A | | 9/1999 | Stefanchik et al. |
| 6,030,386 A | | 2/2000 | Taylor et al. |
| 6,364,888 B1 | | 4/2002 | Niemeyer et al. |
| 7,398,707 B2 | | 7/2008 | Morley et al. |
| 2004/0024385 A1 | * | 2/2004 | Stuart ................................ 606/1 |
| 2004/0097966 A1 | * | 5/2004 | Nakamura .................... 606/130 |
| 2005/0119641 A1 | * | 6/2005 | Jaspers .............................. 606/1 |
| 2007/0129634 A1 | * | 6/2007 | Hickey et al. ................. 600/439 |
| 2008/0314181 A1 | | 12/2008 | Schena |
| 2010/0121347 A1 | * | 5/2010 | Jaspers ........................ 606/130 |
| 2010/0241136 A1 | * | 9/2010 | Doyle et al. .................. 606/130 |
| 2011/0152881 A1 | * | 6/2011 | Conner et al. ................ 606/130 |
| 2012/0083768 A1 | * | 4/2012 | Skora et al. ....................... 606/1 |
| 2012/0158014 A1 | | 6/2012 | Stefanchik et al. |

FOREIGN PATENT DOCUMENTS

| | | |
|---|---|---|
| WO | 2005/039835 A1 | 5/2005 |
| WO | 2008/130235 A2 | 10/2008 |
| WO | 2009126955 A2 | 10/2009 |
| WO | 2010/130817 A1 | 11/2010 |

OTHER PUBLICATIONS

Robot Technology, vol. 3A: Teleoperations and Robotics: Evolution and Development, pp. 67-93, 1986.

International Search Report for Application No. PCT/US2011/064595, issued May 14, 2012. (8 pages).

* cited by examiner

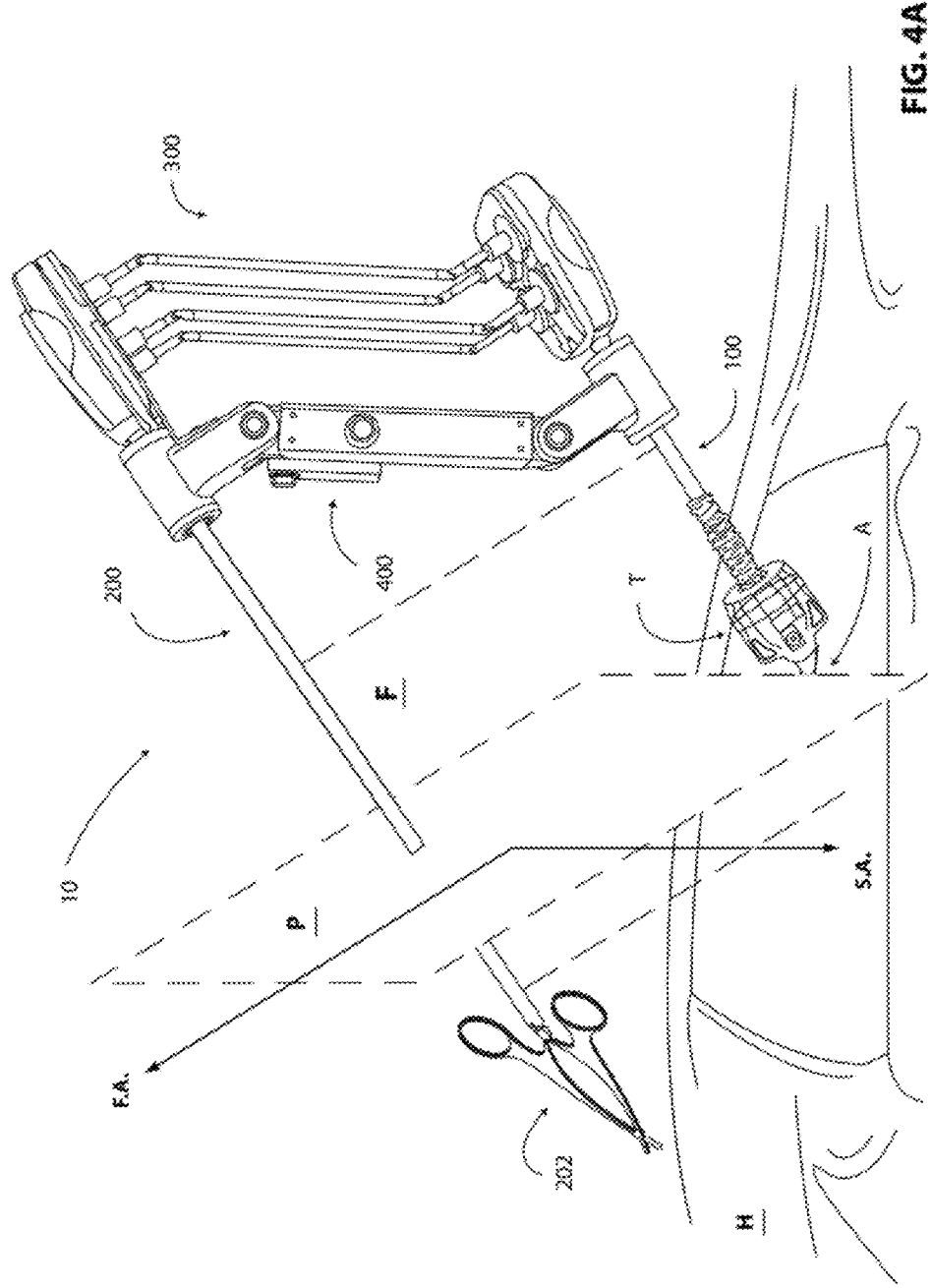

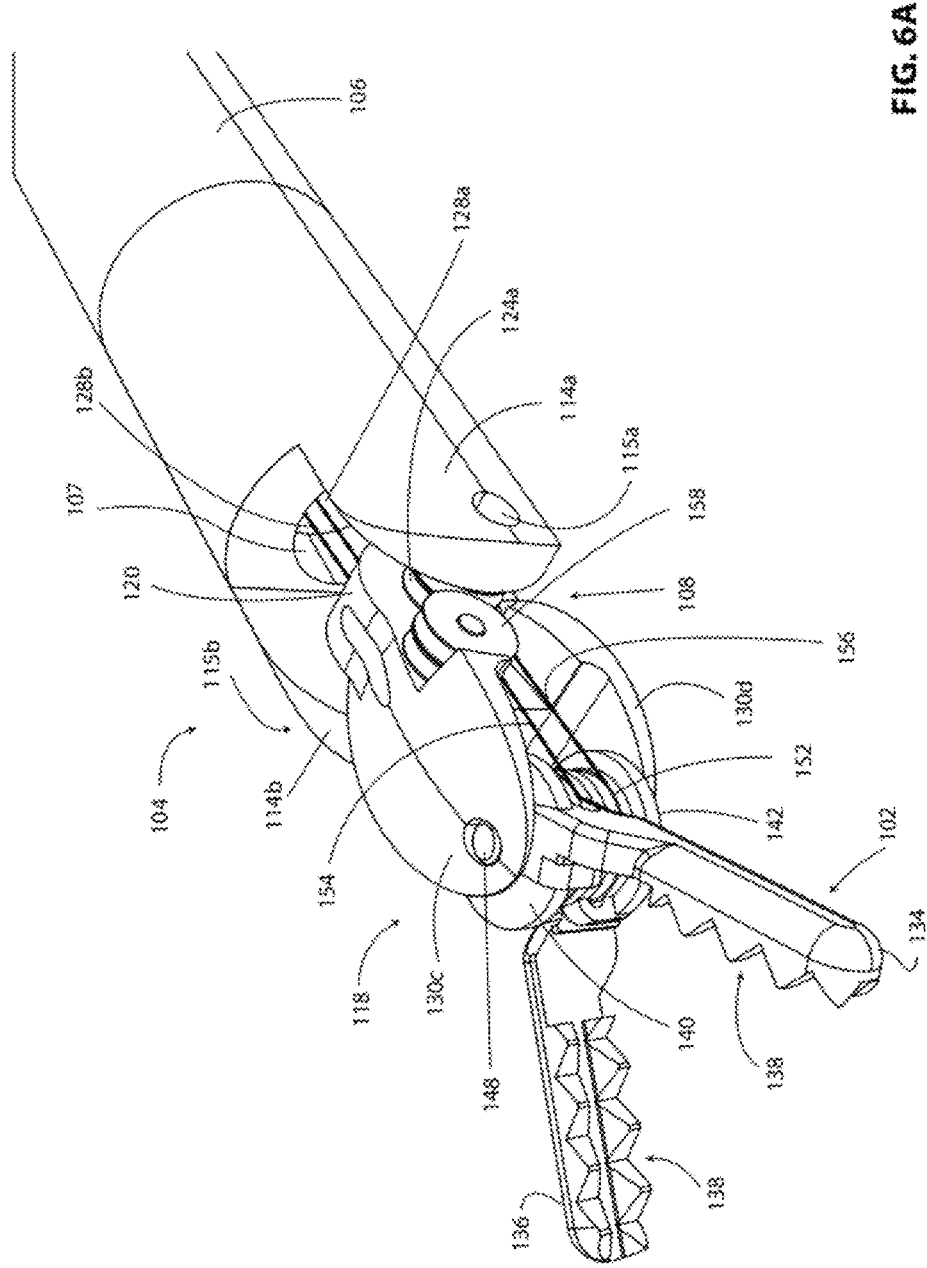

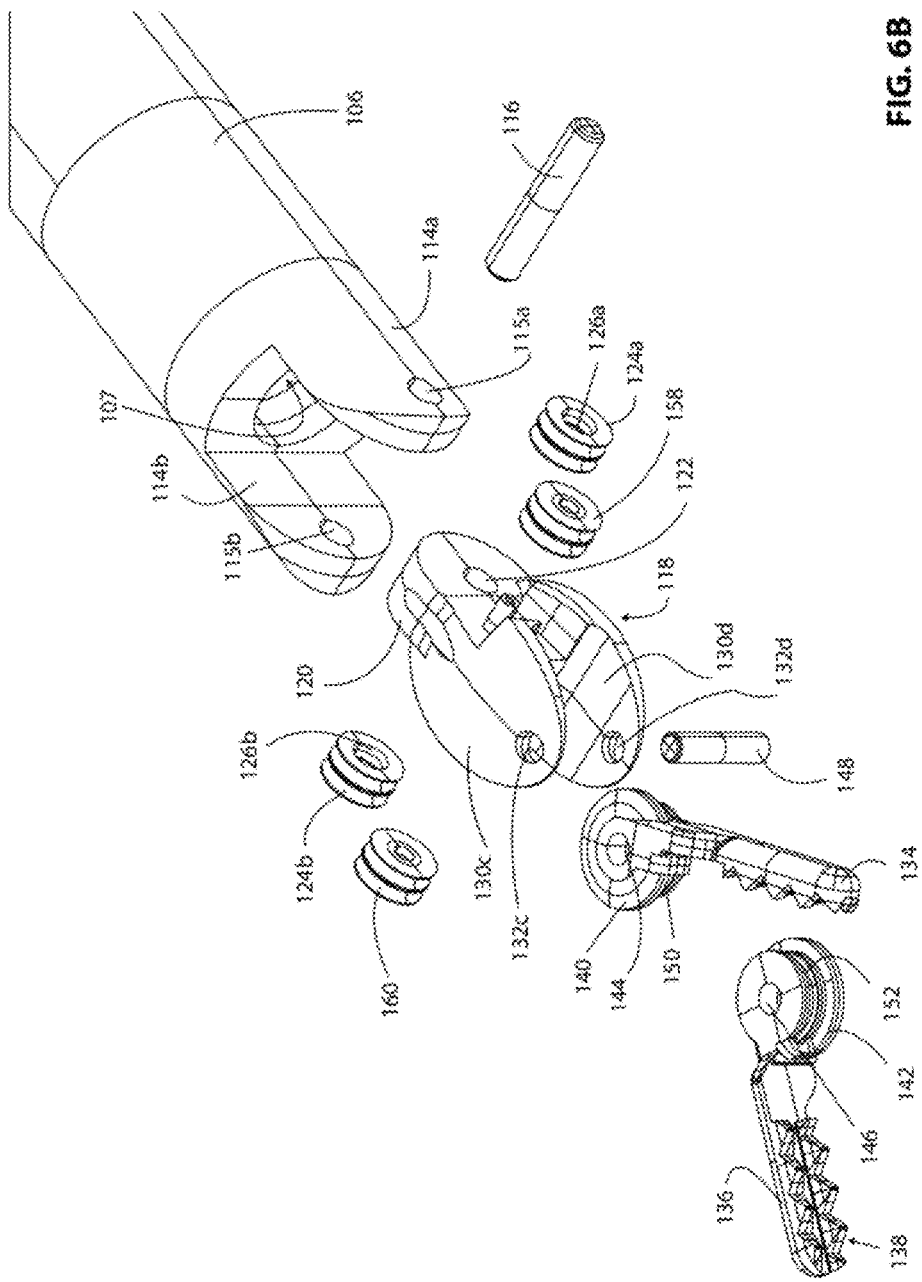

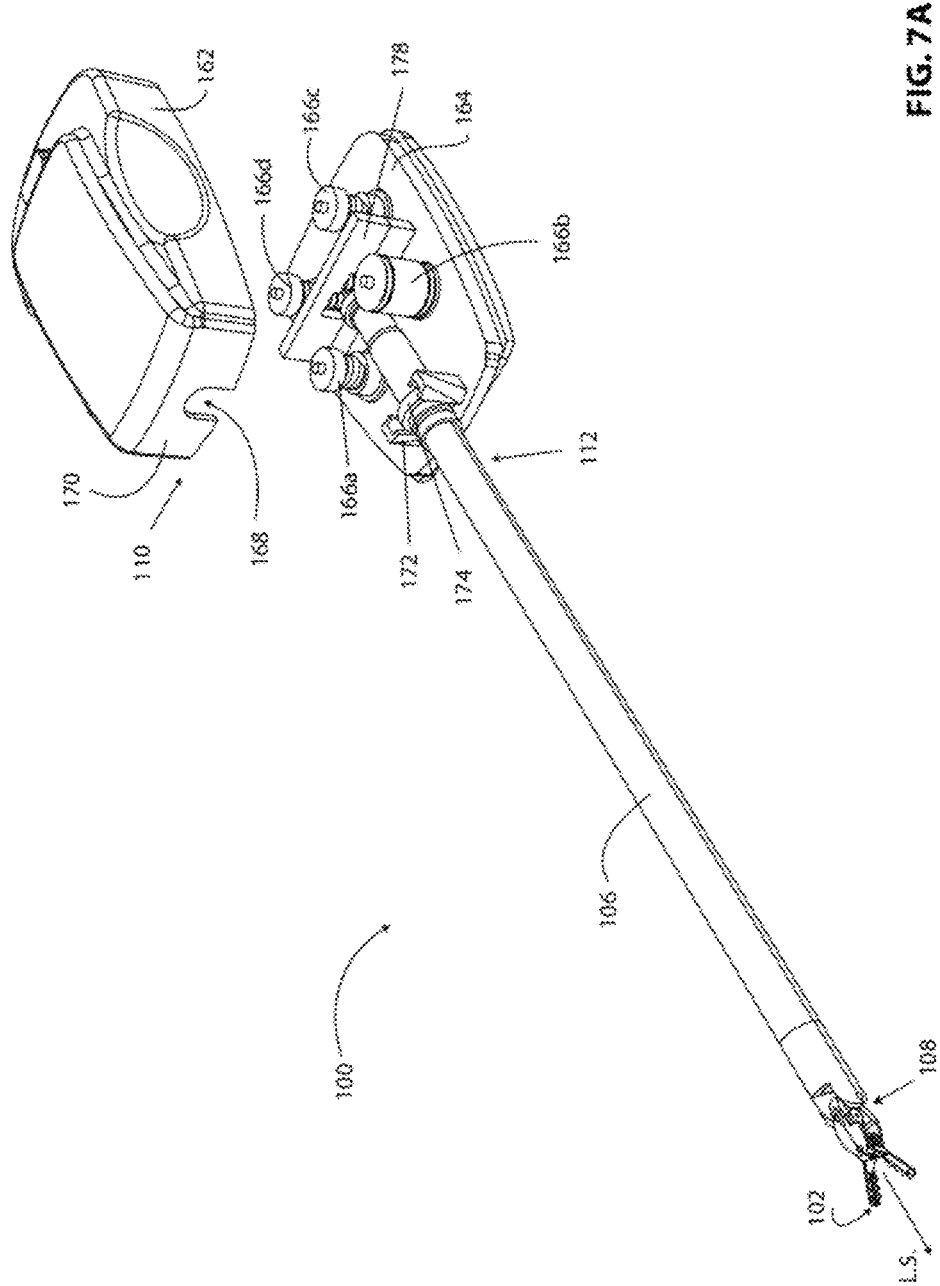

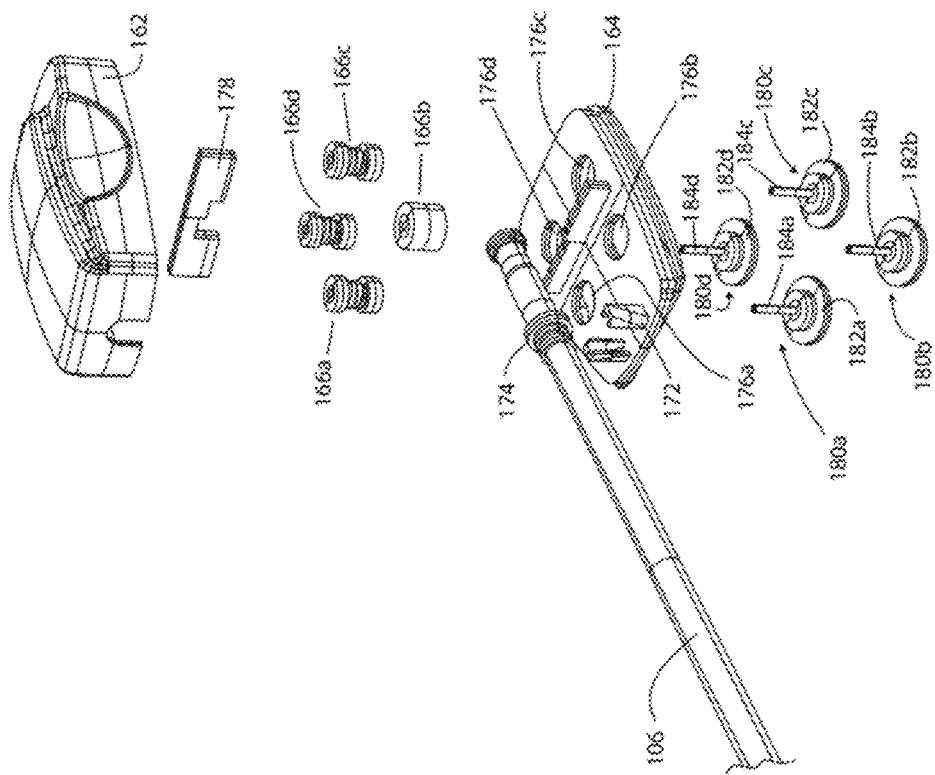

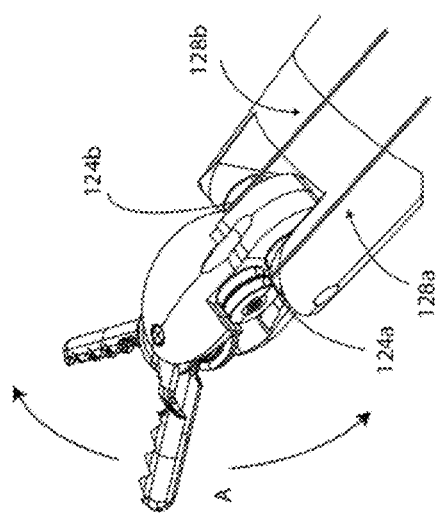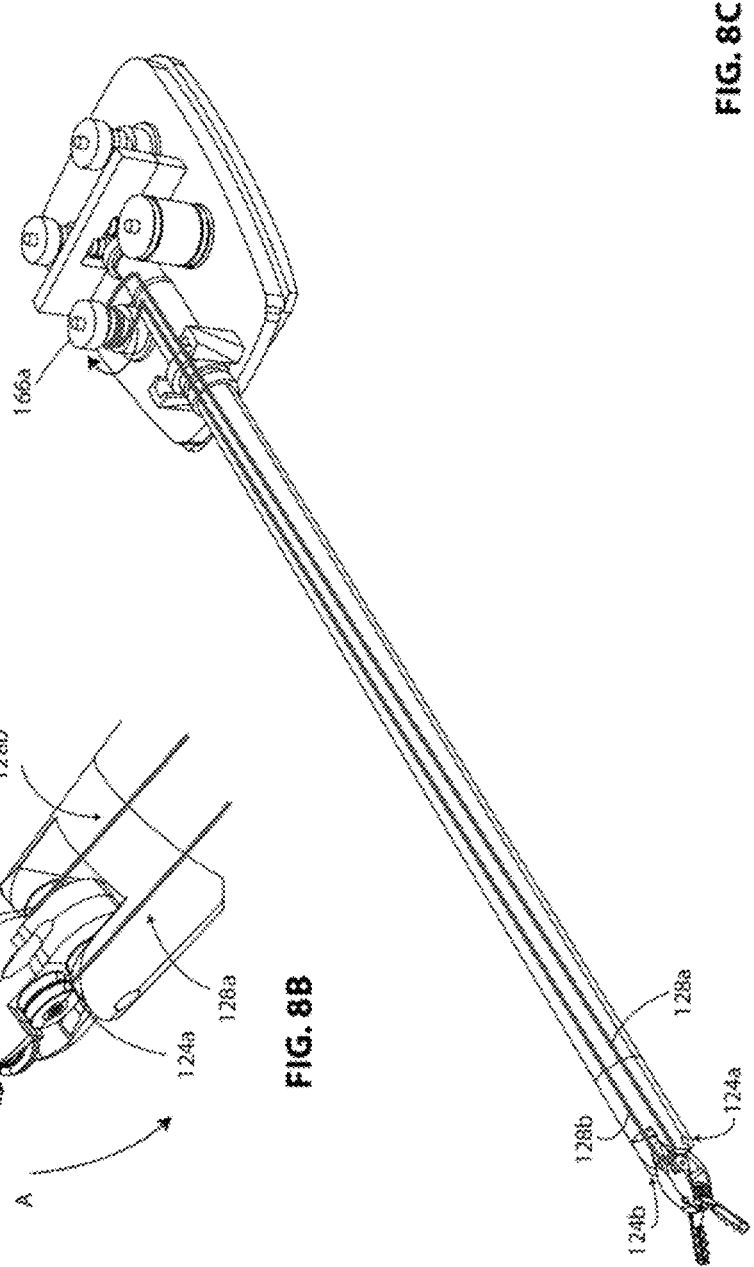

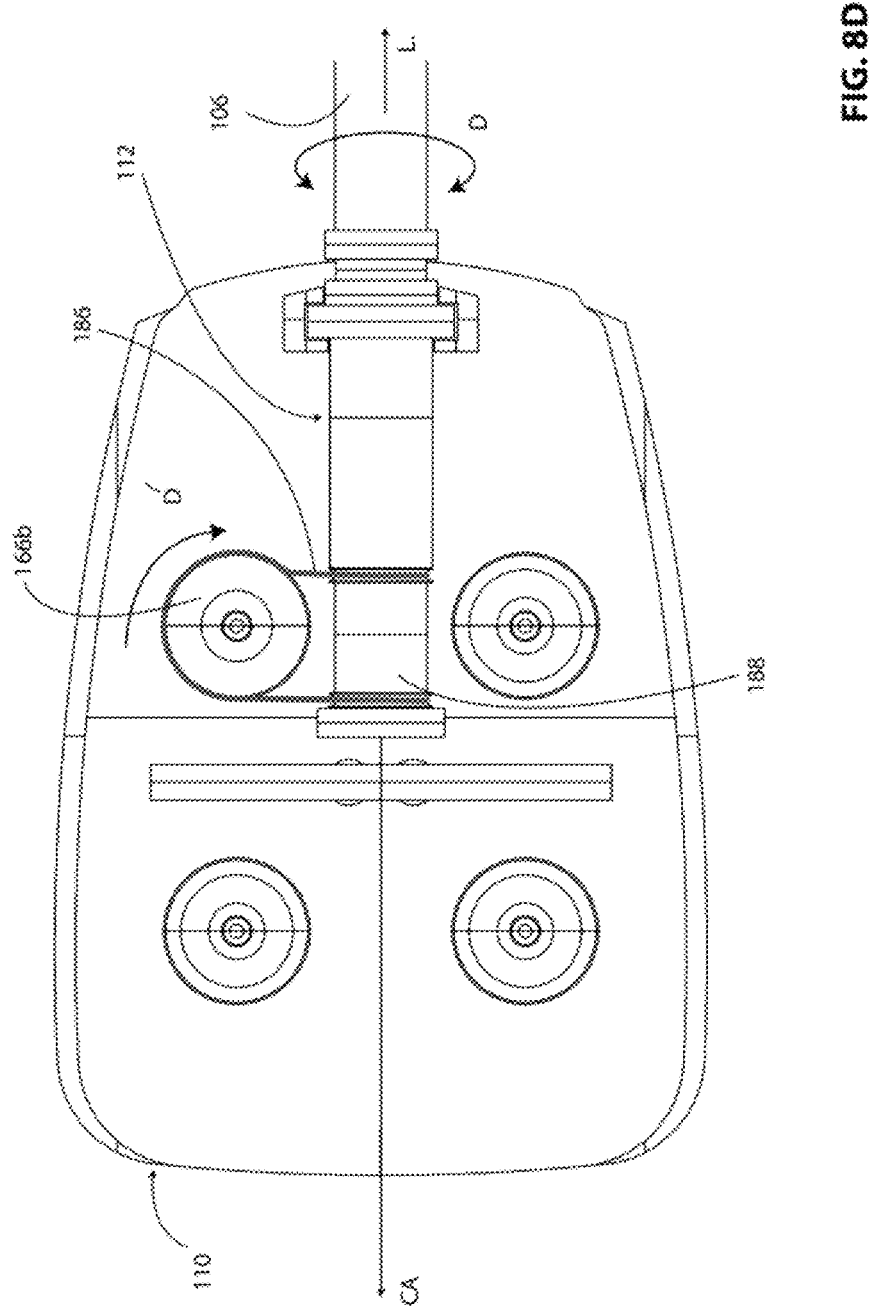

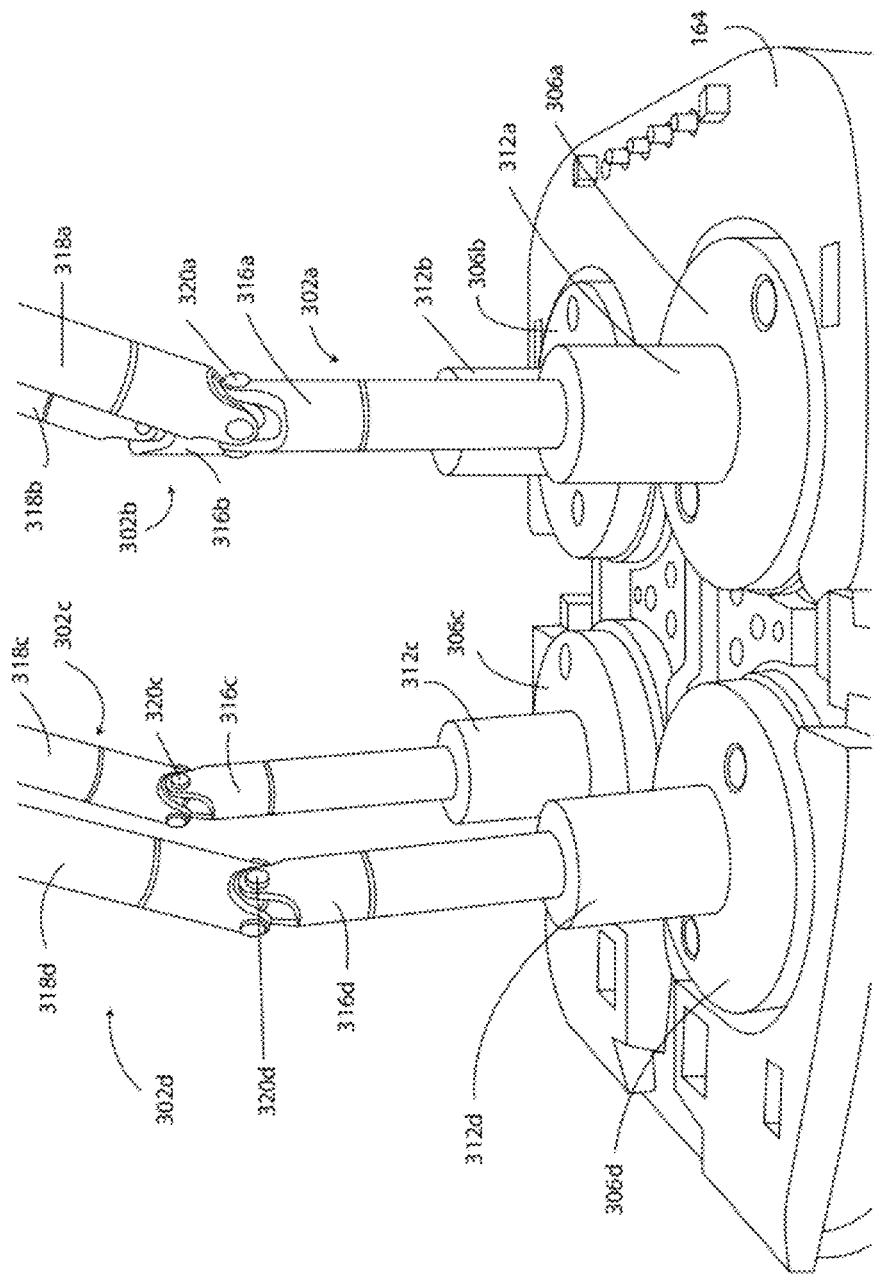

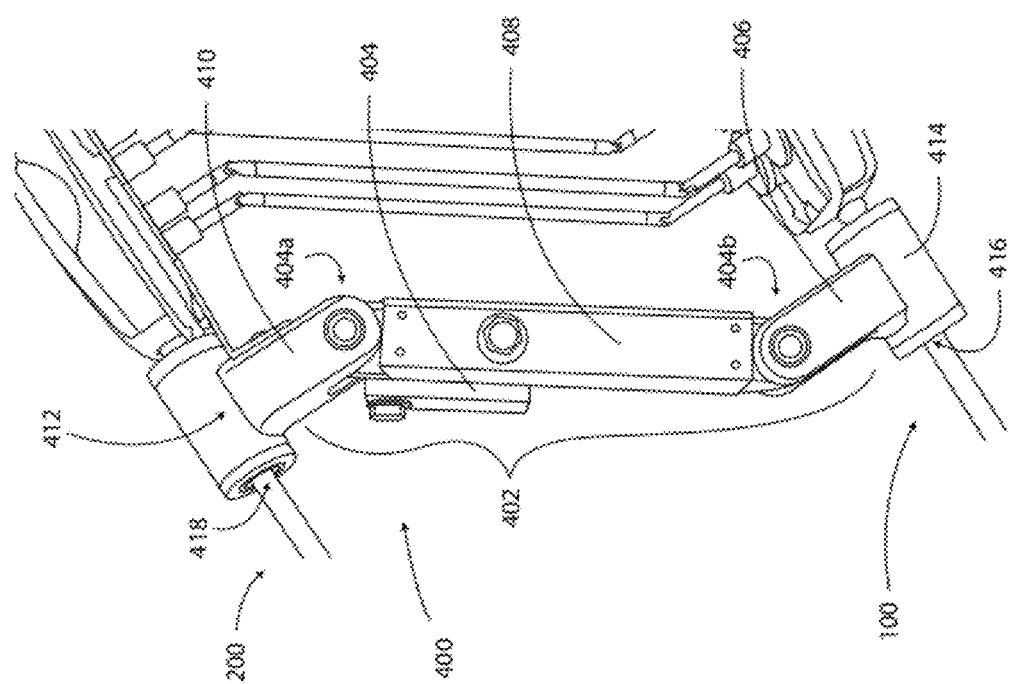

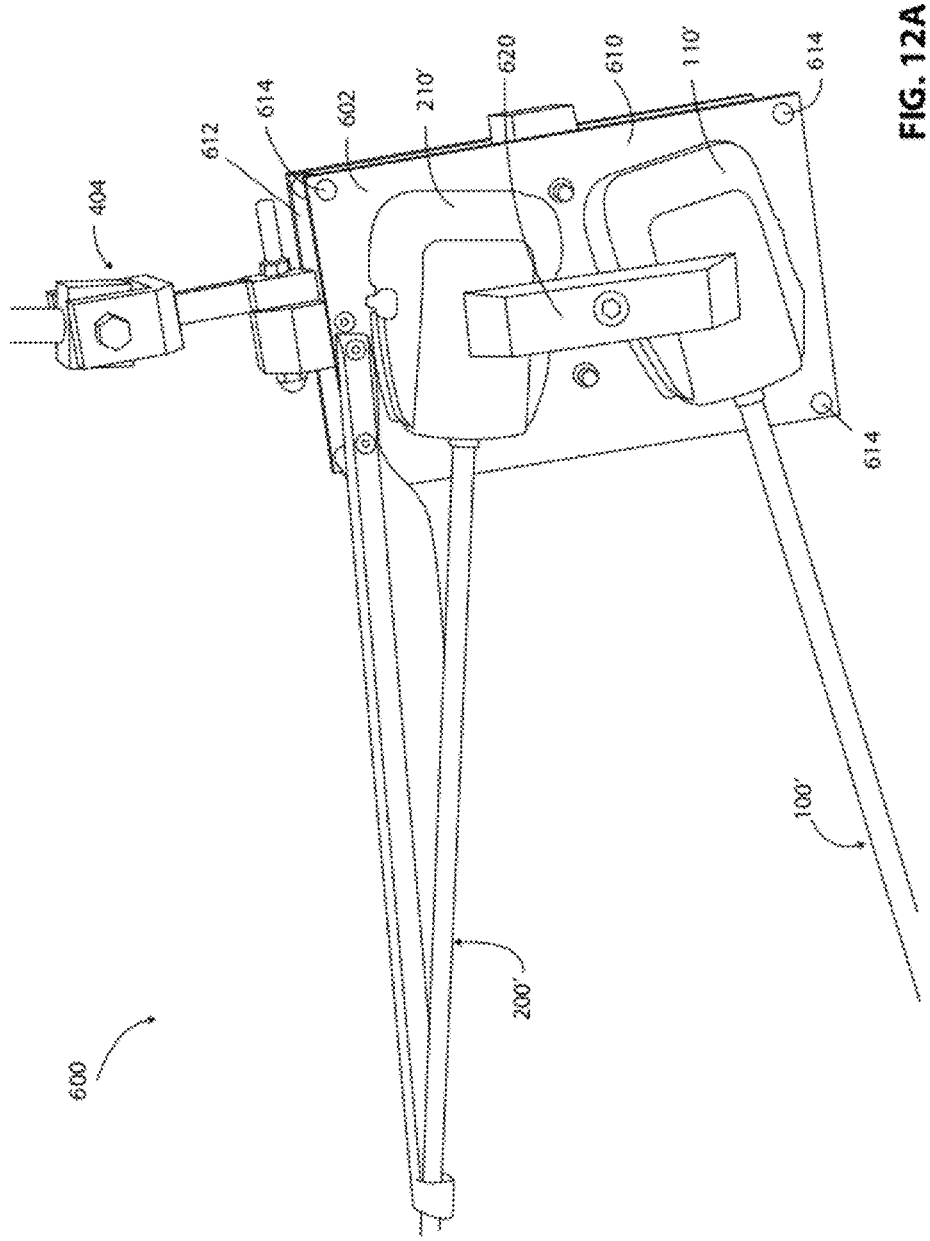

SURGICAL SYSTEM AND METHODS FOR MIMICKED MOTION

FIELD OF THE INVENTION

The present invention relates to methods and devices for controlling movement of an end effector assembly on a distal end of a surgical device, and in particular to methods and devices for causing mimicked motion between a handle and an end effector assembly.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Conventional MIS devices include a handle, an elongate shaft, and an end effector at the distal end for effecting tissue. Motion of the end effector is typically limited to four degrees of freedom (a degree of freedom is the direction in which the end effector can move). Furthermore, motion of the end effector mirrors motion of the handle, such that the operator needs to move the handle in a direction opposite to the desired direction of movement. Shear forces on MIS instruments can also be high, leading to increased operator fatigue.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. There can be no true force feedback given to the surgeon. Another drawback is the high expense to manufacture such systems.

Accordingly, there remains a need for improved methods and devices for controlling movement of a working end of an endoscopic surgical device, and in particular to methods and devices that utilize a mechanical connection to provide for mimicking motion between a handle and an end effector.

SUMMARY OF THE INVENTION

The present invention generally provides surgical methods and devices in which motion of an input tool is mimicked, not mirrored, by motion of an end effector. In one embodiment, a minimally invasive surgical system is provided and can include an elongate master assembly defining a longitudinal axis and having a tool coupled to a forward end thereof, and an elongate slave assembly defining a longitudinal axis and having an end effector coupled to a forward end thereof. In some embodiments, the longitudinal axis of the elongate master assembly and the longitudinal axis of the elongate slave assembly can define a first plane extending therethrough. The system can further include a mechanical coupling system extending between rearward ends of the master assembly and the slave assembly and being configured to transfer corresponding motion of the tool to the end effector such that the end effector mimics motion of the tool. In other embodiments, the first plane can define a first axis parallel to the first plane about which the master and slave assemblies can yaw and a second axis transverse to the first plane. The first axis and the second axis can also define a pivot plane transverse to the first plane. When a forward portion of the slave assembly is inserted into a body cavity through an access point in a tissue surface, the pivot plane can extend through the access point and the tool and the end effector can be positioned forward of the pivot plane.

In some embodiments, when the forward portion of the slave assembly is inserted into a body cavity through an access point in a tissue surface, the mechanical coupling system can be positioned rearward of the pivot plane. In some embodiments, the pivot plane can be perpendicular to the first plane. A stabilizing rod can also be coupled between the master assembly and the slave assembly and can be configured to maintain the master assembly and the slave assembly offset from one another and in a substantially parallel orientation.

While there can be many ways of mounting and controlling the master and slave assemblies, in one embodiment, the surgical system can also include a floating frame coupled to the stabilizing rod and configured to allow simultaneous movement of the master assembly and the slave assembly together in parallel with three translational degrees of freedom that include surging, heaving, and swaying while being rotationally fixed. The floating frame can be coupled to the stabilizing rod through a dual-axis swivel joint that is configured to allow simultaneous movement of the master assembly and the slave assembly together in parallel with two rotational degrees of freedom that include pitching and yawing, while the third rolling rotational degree of freedom can be fixed.

The mechanical coupling system can have many configurations. For example, the mechanical coupling system can be configured to transfer rotation of the tool about a longitudinal axis of the master assembly to the end effector to effect mimicked rotation of the end effector about a longitudinal axis of the slave assembly. In addition, the mechanical coupling system can be configured to transfer pivoting of the tool relative to the master assembly to the end effector to effect mimicked pivoting of the end effector relative to the slave assembly. In some embodiments, the mechanical coupling system can also be configured to transfer opening and closing of the tool to the end effector to effect mimicked opening and closing of the end effector.

In general, the mechanical coupling system can include four linkage assemblies. Each linkage assembly can be configured to transfer to the end effector one of rotating the tool relative to the master assembly, pivoting the tool relative to the master assembly, pivoting a first handle of the tool, and pivoting a second handle of the tool, to thereby effect mimicked motion of the end effector. The mechanical coupling system can also be configured to scale motion of the tool and transfer the scaled motion to the end effector. In some embodiments, a length of the elongate master assembly can be substantially the same as a length of the elongate slave assembly.

In another aspect, a minimally invasive surgical system is provided and can include an elongate master assembly having a forward end with an input tool coupled thereto, a rearward end, and a longitudinal axis extending between the forward and rearward ends. The surgical system can also include an elongate slave assembly having a forward end with an end effector coupled thereto, a rearward end, and a longitudinal axis extending between the forward and rearward ends. The master and slave assemblies can optionally be oriented substantially in parallel with each other. The surgical system can further include a mechanical linkage assembly extending between the rearward ends of the master and slave assemblies such that at least a portion of the linkage assembly is always perpendicular to the longitudinal axes of the master and slave assemblies and at least a portion of the linkage assembly is configured to be at a non-perpendicular angle relative to the longitudinal axes of the master and slave assemblies.

The mechanical linkage assembly can have many configurations and can, for example, be configured to transfer rotation of the tool about the longitudinal axis of the master assembly to the end effector to effect mimicked rotation of the end effector about the longitudinal axis of the slave assembly. The mechanical linkage assembly can also be configured to transfer pivoting of the end tool relative to the master assembly to the end effector to effect mimicked pivoting of the end effector relative to the slave assembly. Further, the mechanical linkage assembly can be configured to transfer opening and closing of the tool to the end effector to effect mimicked opening and closing of the end effector.

In general, the mechanical linkage assembly can include four independent drive rods, each drive rod being configured to transfer to the end effector one of rotating the tool relative to the master assembly, pivoting the tool relative to the master assembly, pivoting a first handle of the tool, and pivoting a second handle of the tool, to thereby effect mimicked movement of the end effector. In addition, the surgical system can also include a stabilizing rod coupled between the master assembly and the slave assembly and configured to maintain the master assembly and the slave assembly in a substantially parallel orientation.

In some embodiments, the surgical system can include a frame coupled to the stabilizing rod through a dual-axis swivel joint. The frame can be configured to allow simultaneous movement of the master assembly and the slave assembly together in parallel with three translational degrees of freedom. The dual-axis swivel joint can be configured to allow simultaneous movement of the master assembly and the slave assembly together in parallel with two rotational degrees of freedom. The three translational degrees of freedom can be surging, heaving, and swaying, and the two rotational degrees of freedom can be pitching and yawing.

In another aspect, a minimally invasive surgical system is provided and can include a shaft assembly having an end effector disposed on a forward end thereof, the shaft assembly being configured to be inserted through an access point in a tissue surface such that the end effector extends into a body cavity. The system can further include a floating frame coupled to the shaft assembly by a dual-axis swivel joint. The floating frame can be configured to move, when it is anchored to a stationary base, with three translational degrees of freedom and the dual-axis swivel joint can be configured to move with two rotational degrees of freedom. In some embodiments, when the shaft assembly is disposed through the access point such that the end effector is disposed within the body cavity, the end effector can be configured to be positioned using one translational degree of freedom from the floating frame and two rotational degrees of freedom from the dual-axis swivel joint.

In a further aspect, a method for performing minimally invasive surgery is provided and can include positioning a slave assembly through a surgical access point in a tissue surface and into a body cavity such that an end effector on a forward end of the slave assembly is within the body cavity. The end effector can be disposed forward of a pivot plane that extends through the access point and has a first axis that is transverse to a longitudinal axis of the slave assembly and a second axis that is perpendicular to the longitudinal axis of the slave assembly about which the slave assembly yaws. The method can further include actuating an input tool coupled to a forward end of a master assembly disposed external to the body cavity to cause mimicked movement of the end effector within the body cavity, the master assembly extending substantially parallel to the slave assembly and the input tool being disposed forward of the pivot plane.

In other embodiments, the method can include rotating the input tool about a longitudinal axis of the master assembly to cause corresponding rotation of the end effector about a longitudinal axis of the slave assembly, and surging the master assembly to cause mimicked surging of the slave assembly through the surgical access point. The method can further include moving the master assembly to cause the slave assembly to pivot about the surgical access point to define a conical volume within the body cavity accessible by the end effector.

In one embodiment, positioning a slave assembly through a surgical access point can include moving a frame coupled to both the master assembly and the slave assembly that allows simultaneous movement of the master and slave assemblies together in parallel with three translational degrees of freedom. The method can further include moving a dual-axis swivel joint coupled between the frame and the master and slave assemblies that allows simultaneous movement of the master and slave assemblies together in parallel with two rotational degrees of freedom. The three translational degrees of freedom can be, for example, surging, heaving, and swaying. The two rotational degrees of freedom can be, for example, pitching, and yawing. The third rolling rotational degree of freedom can be fixed.

In some embodiments, the method can include transferring mimicked movement of the input tool on the master assembly to the end effector on the slave assembly through a mechanical linkage. Further, transferring mimicked movement through the mechanical linkage can include transferring to the end effector rotation of the input tool about a longitudinal axis of the master assembly, as well as pivoting of the input tool relative to the master assembly. In addition, transferring mimicked movement through the mechanical linkage can include transferring opening and closing of the input tool to effect substantially identical opening and closing of the end effector. In one embodiment, movement of the end effector can be different in scale than actuation of the input tool.

In a further aspect, a minimally invasive surgical system is provided and can include a master assembly having a rearward drive system, a forward movable wrist, and a connector extending between the rearward drive system and the forward wrist such that movement of an input tool coupled to the forward wrist is transferred through the cables to cause corresponding movement of the rearward drive system. The surgical system can also include a slave assembly having a rearward drive system, a forward movable wrist, and a plurality of cables extending between the rearward drive system and the forward wrist such that movement of the rearward drive system is transferred through the connector to cause corresponding movement of an end effector coupled to the forward wrist. A mechanical assembly can be directly coupled between the master rearward drive system and the slave rearward drive system such that the mechanical assembly can be configured to transfer motion between the master and slave rearward drive systems. In some embodiments, the slave assembly can be configured to be inserted into a body cavity through an access point in a tissue surface. The master wrist and the slave wrist can be disposed forward of a plane that extends transverse to a longitudinal axis of the slave assembly and through the access point. In some embodiments, the master and slave rearward drive systems can each include pulley systems. In addition, the master and slave connectors can each include a plurality of cables.

The mechanical assembly can have many configurations and can include, for example, four mechanical couplings. The mechanical couplings can be coupled to and move in coordination with the master rearward drive system and the slave rearward drive system. Each mechanical coupling can be configured to transfer from the master assembly to the slave assembly one of rotating the input tool about a longitudinal axis of the master assembly, pivoting the input tool relative to a longitudinal axis of the master assembly, pivoting a first handle of the input tool, and pivoting a second handle of the tool.

In addition, each mechanical coupling can include a superior link, an inferior link, and a middle link, and each link can be coupled together by a universal joint. Each mechanical coupling can further include an inferior coupler and a superior coupler, the inferior coupler being coupled to the slave pulley system and the superior coupler being coupled to the master pulley system. Further, the superior link and the inferior link can each extend along an axis substantially parallel relative to one another and the middle link can extend along an axis transverse to the axes of the superior and inferior links. The superior link, the inferior link, and the middle link can each extend along the same longitudinal axis. In some embodiments, the surgical system can also include a stabilizing rod coupled between the master assembly and the slave assembly and configured to maintain the master assembly and the slave assembly in an offset and substantially parallel orientation.

In another aspect, a minimally invasive surgical system is provided and can include a master assembly having an elongate member and defining a longitudinal axis extending between a forward wrist and a rearward drive housing. The drive housing can have a plurality of drivers disposed therein, and the forward wrist and the plurality of drivers can be operatively connected by a drive connector. The system can also include a slave assembly having an elongate member and defining a longitudinal axis extending between a forward wrist and a rearward drive housing. The drive housing can have a plurality of drivers disposed therein, and the forward wrist and the plurality of drivers can be operatively connected by a drive connector. In some embodiments, the system can further include a mechanical linkage assembly directly coupled between the master drive housing and the slave drive housing and can be configured to transfer mimicked movement of an input tool coupled to the master wrist to an end effector coupled to the slave wrist. A floating frame can be coupled to the master assembly and the slave assembly and can be configured to allow simultaneous movement of the master assembly and the slave assembly together in parallel with three translational degrees of freedom.

In one embodiment, the system can also include a dual-axis swivel joint coupled between the floating frame and the master and slave assemblies and configured to allow simultaneous movement of the master assembly and the slave assembly together in parallel with two rotational degrees of freedom. The dual-axis swivel joint can have a first axis of rotation and a second axis of rotation that define a swivel plane. In some embodiments, the forward wrist of the slave assembly and the forward wrist of the master assembly can be disposed forward of a pivot plane that is parallel with the swivel plane and that extends through an access point when the slave assembly is disposed through the access point.

In another embodiment, the three translational degrees of freedom can be surging, heaving, and swaying, and the two rotational degrees of freedom are pitching and yawing, and wherein the third rolling rotational degree of freedom is fixed. The mechanical linkage assembly can include four independently movable drive rods. The master drive housing and the slave drive housing can each include a pulley housing and the plurality of master drivers and the plurality of slave drivers can each comprise a plurality of movable cables. In some embodiments, the drive rods can be coupled to and move in coordination with the plurality of master pulleys and the plurality of slave pulleys. One of the movable drive rods can be configured to transfer to the end effector through the slave cables rotation of an input tool about a longitudinal axis of the master assembly received from the master cables. In addition, one of the movable drive rods can be configured to transfer to the end effector through the slave cables pivoting of an input tool relative to the master assembly received from the master cables. In some embodiments, two of the movable drive rods can be configured to transfer to the end effector through the slave cables opening and closing of the input tool received from the master cables.

In a further aspect, a method for performing minimally invasive surgery is provided and can include inserting a slave assembly through a surgical access port and into a body cavity such that a slave wrist and an end effector coupled thereto can be disposed within the body cavity. The method can also include manipulating an input tool coupled to a master wrist of a master assembly to transfer motion through a mechanical linkage assembly directly coupled between a master drive system and a slave drive system to cause mimicked movement of the end effector. The master assembly can be disposed outside of the body cavity and can extend parallel to the slave assembly.

In some embodiments, the method can include rotating the input tool about a longitudinal axis of the master assembly to cause corresponding rotation of the end effector about a longitudinal axis of the slave assembly. In addition, the master assembly can be surged to cause mimicked surging of the slave assembly through the surgical access port. Further, manipulating the input tool can move at least one of a plurality of cables of the master drive system, which can include a master pulley system.

In another embodiment, inserting a slave assembly through a surgical access port can include moving a frame coupled to both the master assembly and the slave assembly. Moving the frame can cause simultaneous movement of the master and slave assemblies together in parallel with three degrees of translational freedom. The three degrees of freedom can be surging, heaving, and swaying. In some embodiments, rotating the input tool on the master assembly about a longitudinal axis of the master assembly can cause rotation of a first drive rod of the mechanical linkage assembly to effect corresponding rotation of the end effector on the slave assembly. Further, pivoting the input tool on the master assembly relative to the longitudinal axis of the master assembly can cause rotation of a second drive rod of the mechanical linkage assembly to effect corresponding pivoting of the end effector of the slave assembly. In some embodiments, opening and closing of the input tool of the master assembly can rotate third and fourth drive rods of the mechanical linkage assembly to effect corresponding opening and closing of the end effector of the slave assembly. Moving the input tool can optionally result in scaled movement of the end effector if desired. In general however, a 1:1 ratio between movement of the input tool and movement of the end effector is maintained regardless of the depth of penetration of the end effector within a patient because the input tool and the end effector are of substantially equal distance from the pivot plane.

BRIEF DESCRIPTION OF THE DRAWINGS

The presently disclosed surgical systems and methods will be more fully understood from the following detailed description taken in conjunction with the accompanying drawings, in which:

FIG. 4A is a perspective view of the surgical system of FIG. 2 in use with a patient;

FIG. 6A is a perspective view of an exemplary wrist and end effector mechanism of the slave assembly of FIG. 5;

FIG. 6B is an exploded view of the wrist and end effector mechanism of FIG. 6A;

FIG. 7A is a perspective view of one embodiment of a pulley system associated with the slave assembly of FIG. 5;

FIG. 7B is an exploded view of the pulley system of FIG. 7A;

FIG. 8B is a perspective view of an exemplary wrist cable system for the slave assembly of FIG. 5;

FIG. 8C is another perspective view of the wrist cable system of FIG. 8B;

FIG. 8D is a cross-sectional view of an exemplary slave pulley housing of the slave assembly of FIG. 5 showing a rotational pulley;

FIG. 9C is a perspective view of a portion of the mechanical linkage assembly of FIG. 9A;

FIG. 10A is a perspective view of an exemplary coupling assembly that connects the surgical system and floating frame of FIG. 2;

FIG. 12A is a perspective view of another embodiment of a surgical system for accomplishing mimicked motion;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for controlling movement of an end effector, and in particular for causing mimicked motion between an input tool and an end effector during a surgical procedure. In an exemplary embodiment, a surgical system is provided having a master assembly with an input tool and a slave assembly with an end effector. The master assembly and the slave assembly can be coupled together by a mechanical assembly that is configured to mechanically transfer mimicked, rather than mirrored, motion from the input tool to the end effector. In other words, the end effector will change direction or orientation in a way that is substantially identical to the movement of the input tool, although the motion can be different in scale.

In some embodiments, a floating frame can be utilized with the surgical system. The floating frame can have a counterbalance that allows the surgical system to "float" above a patient and provide a weightless feel to movement of the surgical system. In addition, the floating frame can provide a number of additional degrees of freedom for ease of movement of the surgical system around the patient and/or the operating room.

Terminology

Figure 1:
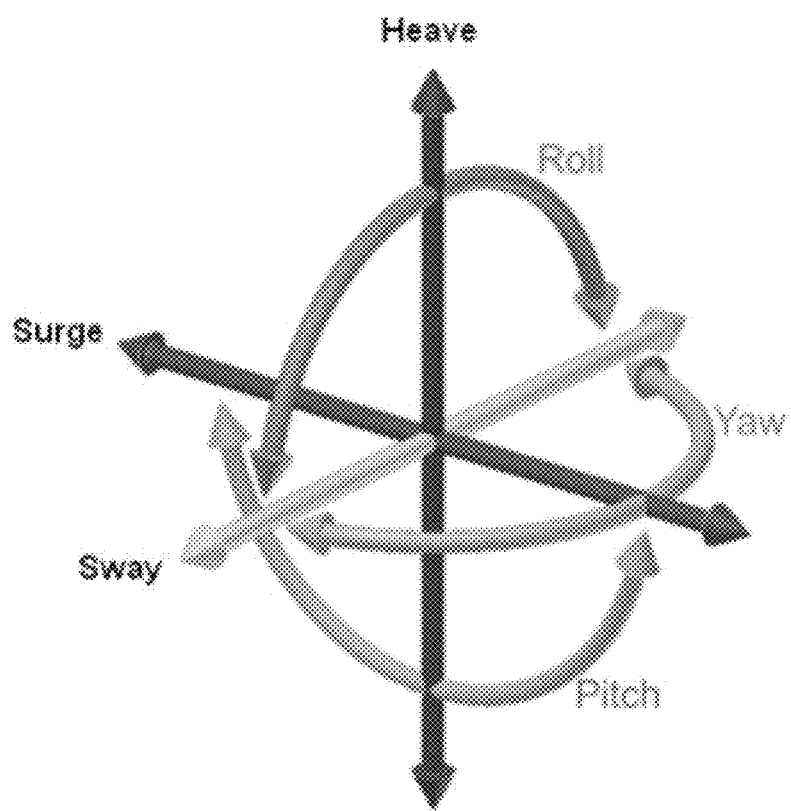
FIG. 1 is a graphical representation of terminology associated with the six degrees of freedom.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational (position) variables (e.g., surge, heave, sway) and by the three rotational (orientation) variables (e.g. Euler angles or roll, pitch, yaw) that describe the position and orientation of a component of a surgical system with respect to a given reference Cartesian frame. As used herein, and as illustrated in FIG. 1, the term surge refers to forward and backward movement, heave refers to movement up and down, and sway refers to movement left and right. With regard to the rotational terms, roll refers to tilting side to side, pitch refers to tilting forward and backward, and yaw refers to turning left and right. In a more general sense, each of the translation terms refers to movement along one of the three axes in a Cartesian frame, and each of the rotational terms refers to rotation about one of the three axes in a Cartesian frame.

In general, and unless otherwise indicated, the frame of reference for rotational movement will be that of the surgical system itself. Each of the rotation axes are perpendicular to each other and remain fixed relative to the surgical system (i.e., move with the surgical system) so that the surgical system always has a pitch, roll, and yaw axis about which the system pitches, rolls, and yaws respectively. The rotational frame of reference may or may not be aligned with the translational frame of reference noted below.

In general, and unless otherwise indicated, the frame of reference for translational movement will be relative to a fixed portion of the floating frame. The floating frame can be generally affixed to a stationary object such as a hospital bed, an operating table, the floor, the ceiling, etc. Translational movement of the surgical system, as well as that of the movable portion of the floating frame, will be relative to this fixed portion and thus generally relative to the bed, floor, ceiling, etc. When translational movement relative to one of the axes in this reference frame is described, it will be referred to as movement along the x, y, or z axis. When the translational movement terms are used (i.e., heave, sway, surge), they will generally refer to movement of the surgical system in that particular direction (up/down, right/left, forward/backward) relative to the translational reference frame. Such movement, however, will not necessarily be along one of the x, y, or z axes.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for the end effector. For redundant kinematic chains, the end effector will have an equal number of degrees of freedom in Cartesian space that will correspond to a combination of translational and rotational motions. Accordingly, the number of joint degrees of freedom can be more than, equal to, or less than six.

With regard to characterizing the position of various components of the surgical system and the floating frame, the terms "forward" and "rearward" will be used. In general, the term "forward" refers to an end of the surgical system that is closest to the end effector and the input tool, and when in use, generally to the end closer to the patient and the user. The term "rearward" refers to an end of the surgical system farthest from the end effector and the input tool, and when in use, generally to the end farther from the patient and the user.

The terminology used herein is not intended to limit the invention. For example, spatially relative terms—such as "superior," "inferior," "beneath," "below," "lower," "above," "upper," "rearward," "forward," and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown or described in various figures. An end effector is the part of a minimally invasive or invasive surgical instrument or assembly that performs a specific surgical function (e.g., forceps/graspers, needle drivers, scissors, electrocautery hooks, staplers, clip appliers/removers, suction tools, irrigation tools, etc.). Any of these exemplary end effectors can be utilized with the surgical system described herein. Further, as noted above, an exemplary end effector is manipulated by an input tool. The input tool can be any tool that allows successful manipulation of the end effector, whether it be a tool similar in shape and style to the end effector, or a tool that is different in shape and style to the end effector. In general, the input tool can be larger than the end effector to facilitate ease of use. For example, the input tool can have finger loops or grips of a size suitable for a user to hold, as shown by the input tool disclosed herein. However, the end effector and the input tool can have any relative size.

As noted briefly above, the slave assembly of the surgical system can be positioned inside a patient's body cavity through an access point in a tissue surface for minimally invasive surgical procedures. Typically cannulas are used to provide a pathway through a tissue surface and to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. It will be appreciated by those skilled in the art that any of the surgical system components disclosed herein can have a functional seal disposed thereon, therein, and/or therearound to prevent and/or reduce insufflation leakage while any portion of the surgical system is disposed through a surgical access port, such as the cannula noted above. The surgical system can also be used in open surgical procedures. As used herein, a surgical access point is a point at which the slave assembly enters a body cavity through a tissue surface, whether through a cannula in a minimally invasive procedure or through an incision in an open procedure.

Surgical System Generally

Figure 2:
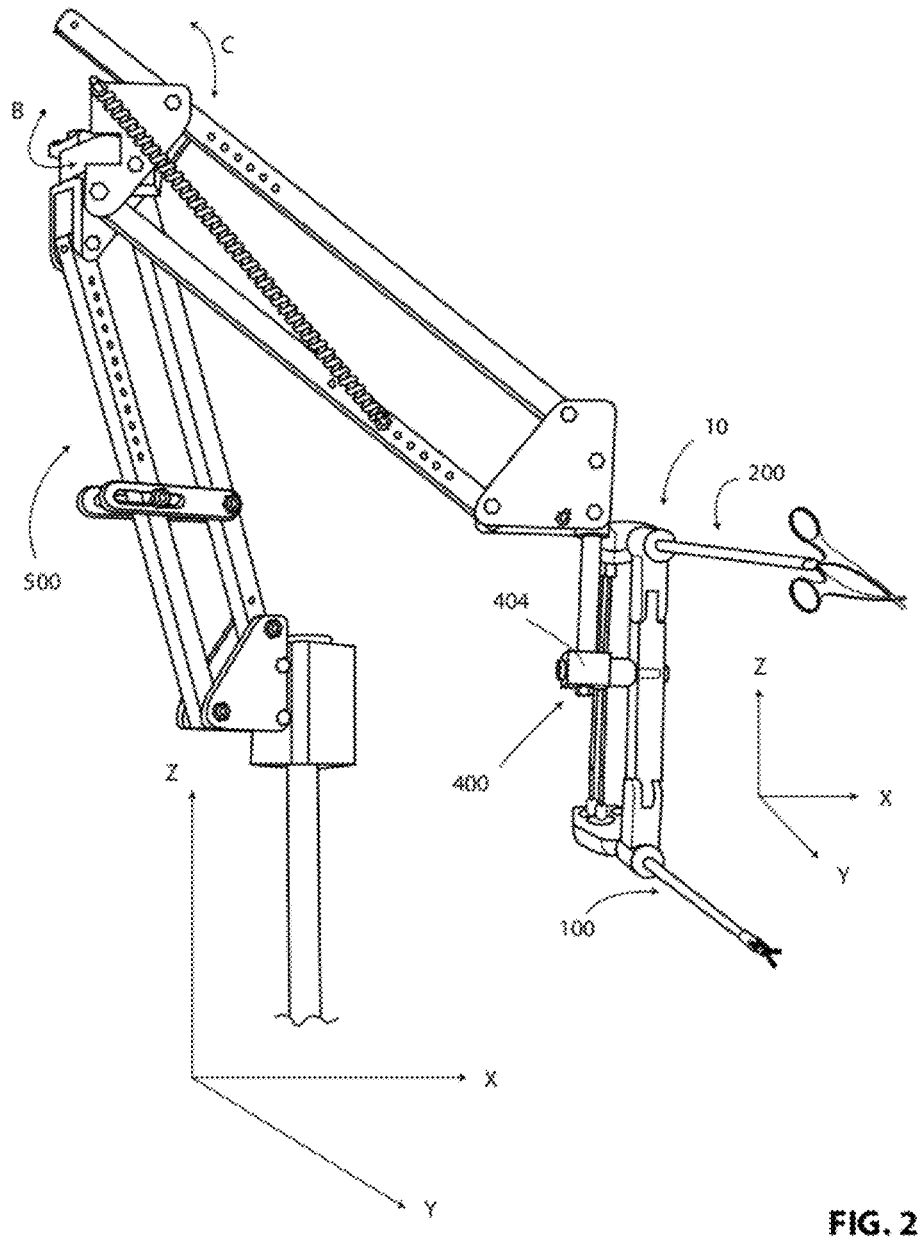
FIG. 2 is a perspective view of one embodiment of a surgical system for accomplishing mimicked motion coupled to floating frame.
Figure 3:
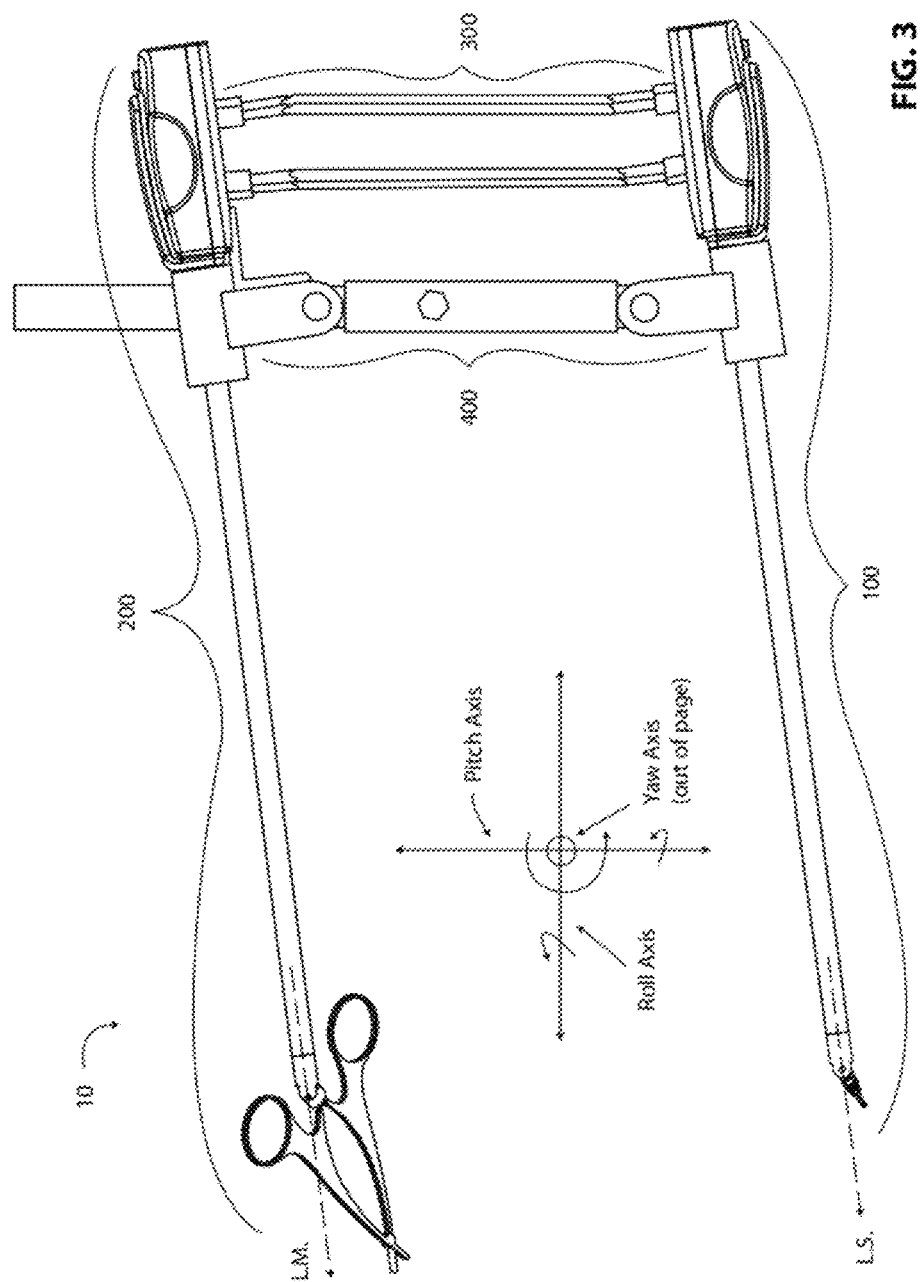
FIG. 3 is a side view of the surgical system of FIG. 2.

One exemplary embodiment of a surgical system 10 is illustrated in FIG. 3. The surgical system 10 can include four main components. First, a master assembly 200 is provided for inputting user directed movement to the surgical system 10. Second, a slave assembly 100 is provided for outputting mimicked movement received from the master assembly 200. Third, a mechanical linkage assembly 300 couples the master assembly 200 and the slave assembly 100 and mechanically transfers movement from the master assembly 200 to the slave assembly 100. Finally, a coupling assembly 400 is provided for maintaining the relative orientation of the master assembly 200 and the slave assembly 100 and for coupling the surgical system 10 to a frame, for example a floating frame 500 illustrated in FIG. 2.

Figure 5:
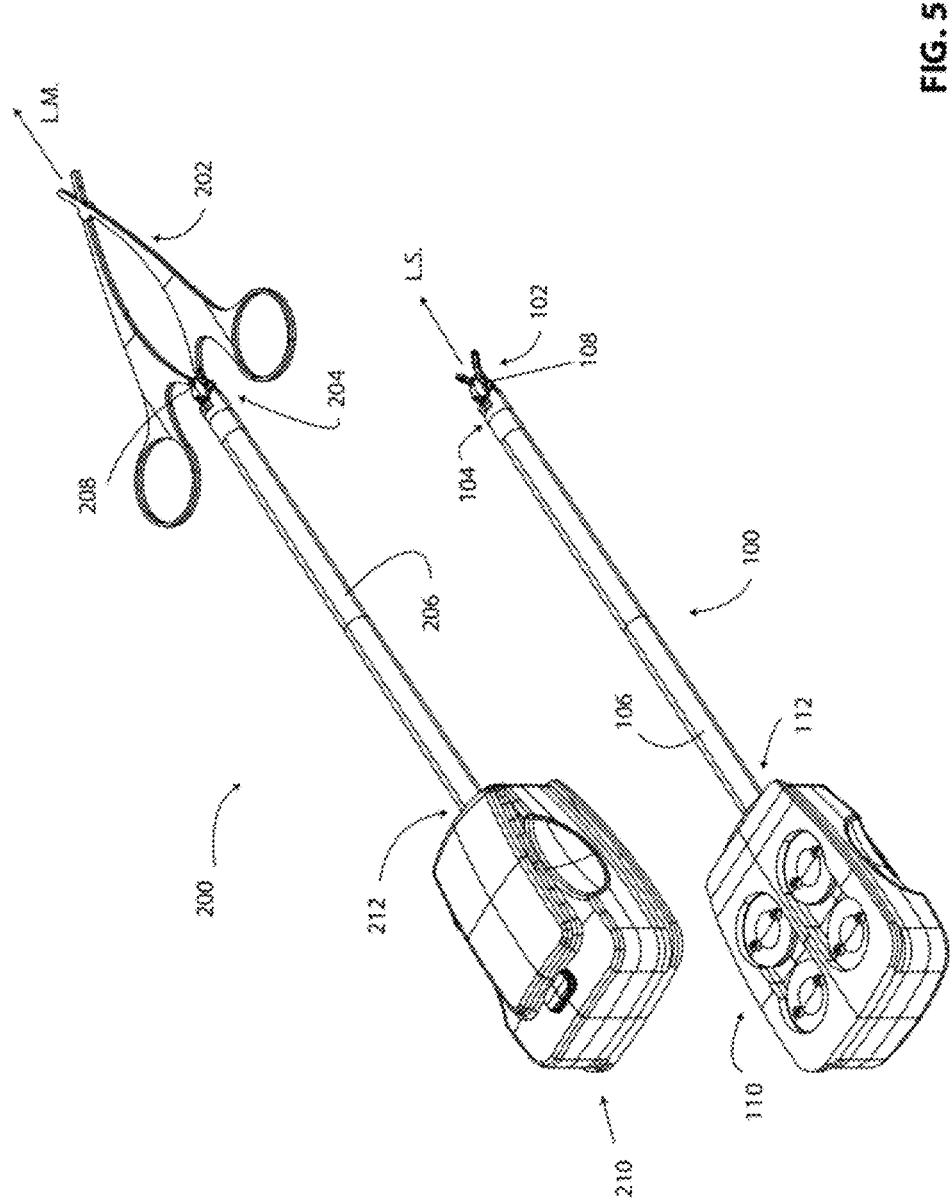
FIG. 5 is a perspective view of exemplary master and slave assemblies of the surgical system of FIG. 2.

The relative positioning of the various components of the surgical system 10 can be important for the transfer of mimicked, rather than mirrored, motion. As shown in FIGS. 3 and 5, in some embodiments, the master assembly 200 can be generally elongate with an input tool 202 disposed on a forward end 204 thereof. Similarly, the slave assembly 100 can be generally elongate with an end effector 102 disposed on a forward end 104 thereof. As shown in FIG. 3, the master assembly 200 and the slave assembly 100 can be oriented substantially parallel to one another. The mechanical linkage assembly 400 can extend between the master assembly 200 and the slave assembly 100 and can generally be oriented perpendicularly thereto, although certain portions of the mechanical linkage assembly 400 can extend non-perpendicularly to the assemblies 100, 200 as will be described below. The coupling assembly 500 can also extend generally perpendicularly to the master assembly 200 and the slave assembly 100 and generally in parallel with the mechanical linkage assembly 400. The coupling assembly 500 can maintain the parallel orientation of the master assembly 200 and the slave assembly 100. A person skilled in the art will appreciate that the orientation of the various components are exemplary in nature and that the components can be oriented at various angles relative to one another if desired.

In use, the positioning and orientation of the four major components of the surgical system 10 as described above results in the transfer of mimicked motion between the input tool 202 and the end effector 102. As shown in FIG. 4A, the input tool 202 and the end effector 102 (not shown), and thus a user and the patient H, are on the same forward end of the surgical system 10. When the end effector 102 of the slave assembly 100 is disposed within a body cavity during use as shown in FIG. 4, the slave assembly 100 can extend through a surgical access point A in a tissue surface such that the surgical system 10 can pivot about this access point A. Both the end effector 102 and the input tool 202 are positioned forward of a pivot plane P that extends through the access point A. As shown in FIG. 4A, the pivot plane P can have a first axis F.A. that is parallel with a first plane F defined by the longitudinal axes of the slave assembly 100 and the master assembly 200 and about which the surgical system 10 yaws. The pivot plane P can also have a second axis S.A. that is transverse to the first plane F such that the pivot plane P extends transverse to the first plane F. Additional details of the pivot plane P will be described in more detail below with regard to FIGS. 10B and 10D. Because of this configuration, the master assembly 200 and the slave assembly 100 are capable of mimicked motion. For example, when a user changes the pitch of the master assembly 200 downward, the slave assembly 100 identically pitches downward. If the input tool 202 were instead on the rearward side of the pivot plane P while the end effector 102 remained on the forward side, the pitch change would be mirrored, rather than mimicked, and the end effector 102 would pitch upward when the input tool 202 was pitched downward. Similarly, if a user changes the yaw of the master assembly 200 rightward, the slave assembly 100 identically yaws rightward. However if the input tool 202 were on the rearward side of the pivot plane P, the end effector 102 would yaw leftward in response to the input tool 202 yawing rightward. The mimicked movement of the surgical system 10 provides a more natural way for a user to perform surgical procedures since a user's movements are transferred to the end effector 102 identically.

Surgical System Detail

The master assembly 200 and the slave assembly 100 of the surgical system 10 are shown in more detail in FIG. 5. In some embodiments, the slave assembly 100 can include a slave arm 106 extending between a forward wrist 108 and a rearward drive housing, such as a rearward pulley housing 110, while the master assembly 200 can include a master arm 206 extending between a forward wrist 208 and a rearward drive housing such as a rearward pulley housing 210. The slave assembly 100 and the master assembly 200 can each have a size that is substantially the same, and thus the arms 106, 206 can have a length that is substantially the same. A connector system, such as a plurality of cables described in detail later, can extend through the elongate arms 106, 206 between the wrists 108, 208 and the pulley housings 110, 210 and can be configured to communicate movement at the wrists 108, 208 to drivers, such as pulleys disposed within the pulley housings 110, 210. The drivers and/or pulleys in the pulley housings 110, 210 can generally be configured to output and/or receive movement to/from the mechanical linkage system 300 coupled thereto. As will be appreciated by those skilled in the art, the pulley housing, pulleys, and cable systems described herein can generally be replaced by any mechanical drive system known in the art, such as a gear system or other mechanism. For example, the pulley housings 110, 210 can be replaced by drive housings, the pulleys can be replaced by drivers, and the pulley cables can be replaced by any connectors known in the art, such as rack and pinions, gears, and/or belts.

The master assembly 200 and the slave assembly 100 can be substantially identical in structure apart from the input tool 202 and the end effector 102. Thus only one assembly need be described in detail. The slave assembly 100 will thus be described in detail with reference numbers in the 100s. An identical and corresponding component in the master assembly 200 will have a reference number in the 200s, with the last two digits being identical to the corresponding slave assembly reference number. For example, the slave wrist has a reference number "108" while the master wrist has a reference number "208." This convention will be followed throughout the description.

The arm 106 and the wrist 108 of the slave assembly 100 are shown in more detail in FIGS. 6A-7A. In some embodiments, the arm 106 of the slave assembly 100 can be a substantially rigid elongate member with a bore 107 extending therethrough and having a length substantially greater than a diameter thereof. The arm 106 can define a central longitudinal axis L.S. extending between the forward end 104 and a rearward end 112 thereof. In some embodiments, the rearward end 112 of the arm 106 can extend into and terminate within the pulley housing 110. The opposite, forward end 104 of the arm 106 can couple to the wrist 108 through the use of a clevis joint, as shown in FIGS. 6A and 6B. In particular, the forward end 104 of the arm 106 can have two extension portions 114a, 114b that form a clevis for receiving the wrist 108. Each extension portion 114a, 114b can have an opening 115a, 115b formed laterally therethrough for receiving a clevis pin 116.

As noted above, the forward wrist 108 can be coupled between the forward end 104 of the arm 106 and the end effector 102. The wrist 108 can take many forms suitable for coupling the arm 106 and the end effector 102, and in the illustrated embodiment it can generally include a frame 118 coupled to a plurality of pulleys for communicating movement of the end effector 102 to pulleys within the pulley housing 110. The wrist frame 118 can have, for example, a tang 120 formed at its rearward end with an opening 122 formed laterally therethrough that can be aligned with the openings 115a, 115b formed in the extension portions 114a, 114b for receiving the clevis pin 116. The coupling between the wrist tang 118 and the extension portions 114a, 114b can allow the wrist 108 to rotate about the clevis pin 116, thereby allowing the wrist 108 and the end effector 102 to pitch (i.e., to pivot) relative to the arm, as shown by arrow A in FIG. 8B.

The wrist 108 can include any number of pulleys to accomplish desired motion. Two of the plurality of pulleys within the wrist 108 can be positioned within the clevis joint adjacent to the tang 120 of the wrist frame 118. In particular, one pulley 124a can be positioned between the tang 120 and the extension portion 114a, and another pulley 124b can be positioned between the tang 120 and the opposite extension portion 114b. The pulleys 124a, 124b can have corresponding openings 126a, 126b formed therethrough for receiving the clevis pin 116 that extends through the tang 120 and the extension portions 114a, 114b. The pulleys 124a, 124b can each receive a cable 128a, 128b that transfers pitching motion to the wrist 108, i.e., when the pulleys 124a, 124b are rotated by the cables 128a, 128b in a first direction, the wrist 108 and the end effector 102 pitch in the same first direction.

The wrist frame 118 can also have two extension portions 130c, 130d extending forwardly from the tang 120 and forming another clevis joint at its forward end for coupling to the end effector 102. Each of the extension portions 130c, 130d can have an opening 132c, 132d formed laterally therethrough in a direction perpendicular to the lateral opening 122 formed in the tang 118 for receiving the clevis pin 116. In the illustrated embodiment, the end effector 102 has opposed jaws 134, 136 configured to open and close relative to one another and each having a plurality of gripping teeth 138 formed thereon. Each jaw member 134, 136 can have a tang 140, 142 formed on a rearward end thereof with a lateral opening 144, 146 formed therethrough for receiving the clevis pin 148. In the illustrated embodiment, each tang 140, 142 can also include a pulley 150, 152 rigidly disposed thereon for receiving a corresponding cable 154, 156 to communicate movement to each jaw member 134, 136.

When assembled, the tangs 140, 142 of the jaw members 134, 136 can be positioned adjacent to each other between the extension portions 130c, 130d of the wrist frame 118 such that the two pulleys 150, 152 are positioned in contact with one another. Due to each pulley 150, 152 receiving independently movable cables 154, 156, each jaw member 134, 136 can be configured to rotate about the clevis pin 148 independently of the other jaw member 136, 134 such that each yaws relative to the end effector 102 and the arm 106. In other words, since the end effector 102 is configured to pitch relative to the arm 106, and since the jaw members 134, 136 each pivot in a direction opposite to the direction that the end effector 102 pitches, the jaw members 134, 136 can be considered to yaw relative to the arm 106 and relative to the end effector 102. The wrist 108 can include two additional pulleys 158, 160 disposed on opposite sides thereof and oriented in the same direction as the wrist pulleys 124a, 124b and in the opposite direction to the jaw member pulleys 150, 152. The pulleys 158, 160 can receive the cables 154, 156 from the jaw member pulleys 150, 152 and can orient the cables 154, 156 in the same direction as the wrist cables 128a, 128b to extend through the tubular arm 106.

surgical system pulley housing

As noted above, the rearward end 112 of the arm 106 can extend into the pulley housing 110 that generally holds a plurality of rearward pulleys. In the illustrated embodiment shown in FIGS. 7A and 7B, there are four rearward pulleys 166a, 166b, 166c, 166d (jointly "166") that receive the cables 128a, 128b, 154, 156 from the wrist 108 and a cable 186 from the arm 106 (shown in FIG. 8C and described below) and transfer movement to and/or from the mechanical linkage assembly 300.

The pulley housing 110 can take many forms, but in the illustrated embodiment, the pulley housing 110 is in the form of a substantially rectangular box with a housing cover 162 and a housing base 164 that couple together to enclose the rearward end 112 of the arm 106 and the pulleys 166. The housing cover 162 and the housing base 164 can be coupled together by any mechanism known in the art including, but not limited to, a press fit, interference fit, fasteners, adhesives, etc. The housing cover 162 can include an opening 168 formed in a forward sidewall 170 thereof for receiving the arm 106 therethrough while allowing rotation of the arm 106 relative thereto.

The housing base 164 can generally be configured to seat and retain the pulleys 166. Thus, the housing base 164 can include a slotted brace 172 for seating a rearward flange 174 of the arm 106. The housing base 164 can also include four openings 176a, 176b, 176c, 176d (jointly "176") extending therethrough for seating the four pulleys 166. Four connector plates 180a, 180b, 180c, 180d ("jointly "180") can seat the pulleys 166 within the openings 176. Each connector plate 180 can have a base 182a, 182b, 182c, 182d (jointly "182") with a spool rod 184a, 184b, 184c, 184d (jointly "184") extending perpendicularly therefrom for seating the pulleys 166. The pulleys 166 can be fixedly and/or rigidly coupled to their corresponding connector plates 180 so that neither the pulleys 166 nor the plates 180 are capable of rotation relative to each other. A support wall 178 can extend upward from the housing base 164 between the pulleys 166 for separating the cables 154, 156 for the rearward pulleys 166c, 166d from the cables 128a, 128b, 186 for the forward pulleys 166a, 166b and for guiding the cables 128a, 128c, and 128d into the arm 106.

Figure 8A:
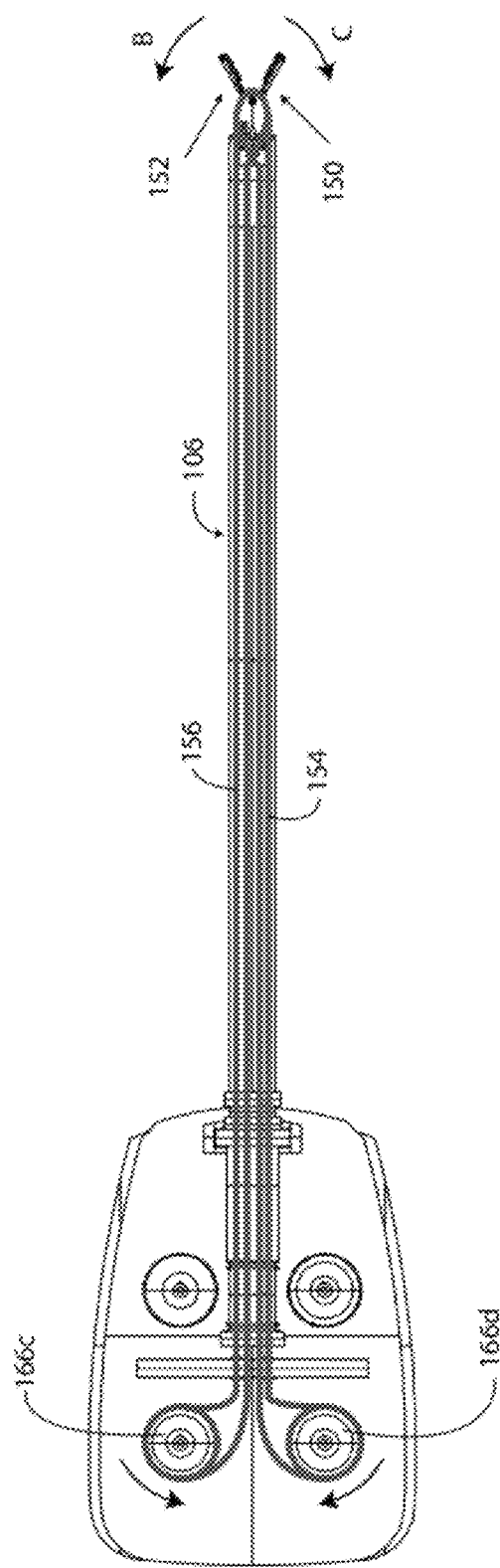
FIG. 8A is a cross-sectional view of the slave assembly of FIG. 5 showing an exemplary end effector cable system.

Each of the four pulleys 166 in the pulley housing 110 can be configured to transfer a specific type of movement to and/or from the mechanical linkage assembly 300. Thus, as shown in FIGS. 8A-8C, in general, the cables 128a, 128b, 154, 156 for transferring movement to and from the wrist 108 can extend from the pulleys 124a, 124b, 150, 152, respectively, at the wrist 108 to three of the pulleys 166a, 166c, 166d in the pulley housing 110 (cables 128a, 128b both extend to pulley 166a). For example, as shown in FIG. 8C, the cables 128a, 128b extending from each of the wrist pulleys 124a, 124b can extend through the arm 106 to the pulley 166a such that pitching of the wrist 108 (shown by arrow A in FIG. 8B) results in rotation of the pulley 166a. In addition, as shown in FIG. 8A, the cable 154 can extend between the jaw member pulley 150 and the pulley 166d in the housing 110. Likewise, the cable 156 can extend between the other jaw member pulley 152 and the pulley 166c in the housing 110. Each of the cables 154, 156 can be pulled by rotation of their corresponding pulley 166d, 166c to cause yawing movement of the jaws 134, 136 as shown by arrows B and C.

The fourth pulley 166b in the pulley housing 110, shown in FIG. 8D, can receive the cable 186 from a rotational pulley 188 disposed on the rearward end 112 of the arm 106. The rotational pulley 188 can have a central axis C.A. that is co-linear with the central longitudinal axis of the arm L.S. The cable 186 can extend from the rotational pulley 188 to the pulley 166b such that as the arm 106 rotates as indicated by arrow D, the cable 186 functions to rotate the corresponding fourth pulley 166b in a corresponding direction D'.

Figure 9A:
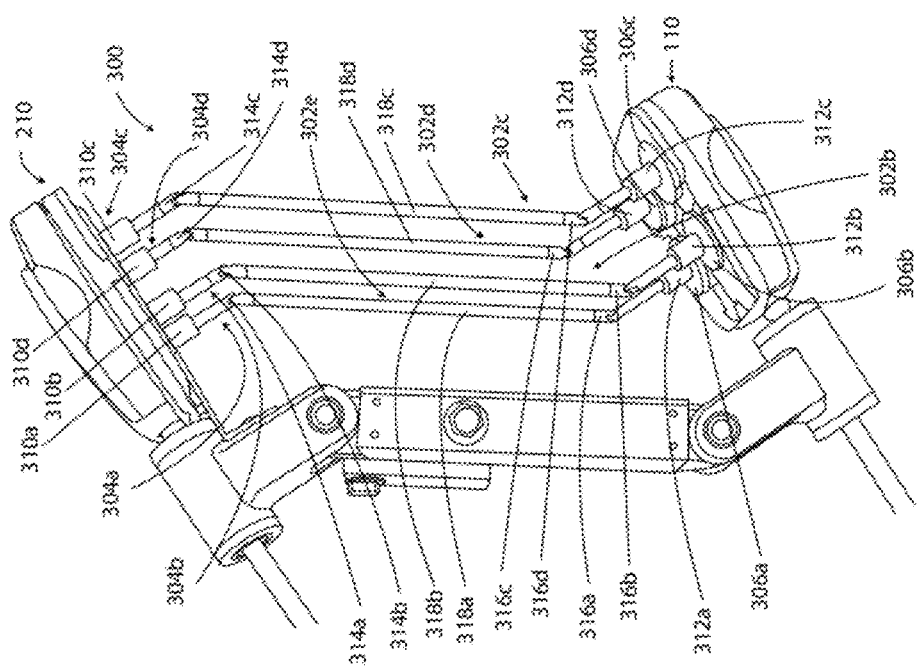
FIG. 9A is a perspective view of an exemplary mechanical linkage assembly of the surgical system of FIG. 2.

As noted above, each of the four pulleys 166 within the housing 110 can be rigidly coupled to the connector plates 180 that extend through the housing base 164. This allows the pulleys 166 to be coupled to the mechanical linkage assembly 300 through their corresponding connector plates 180 as shown in FIG. 9A and as will be described in more detail below. In this way, rotation of the pulleys 166 results in corresponding rotation of the mechanical linkage assembly 300 and vice versa, as will also be described in detail below.

As noted above, the master assembly 200 is substantially identical to the above-described slave assembly 100 except that the input tool 202 is coupled to the forward wrist 204 rather than the end effector 102. It will be appreciated by those having ordinary skill in the art that the above-described arm/wrist/pulley system is only exemplary in nature. There are a number of robotic arms that can be used as a master/slave assembly, and there are a number of additional joints and/or wrists that can be included on a particular arm to provide jointed movement of the arm. Non-limiting examples of such components can be found in U.S. Pat. No. 5,702,408 Wales et al., incorporated by reference in their entireties.

Surgical System Mechanical Linkage Assembly

Figure 9B:
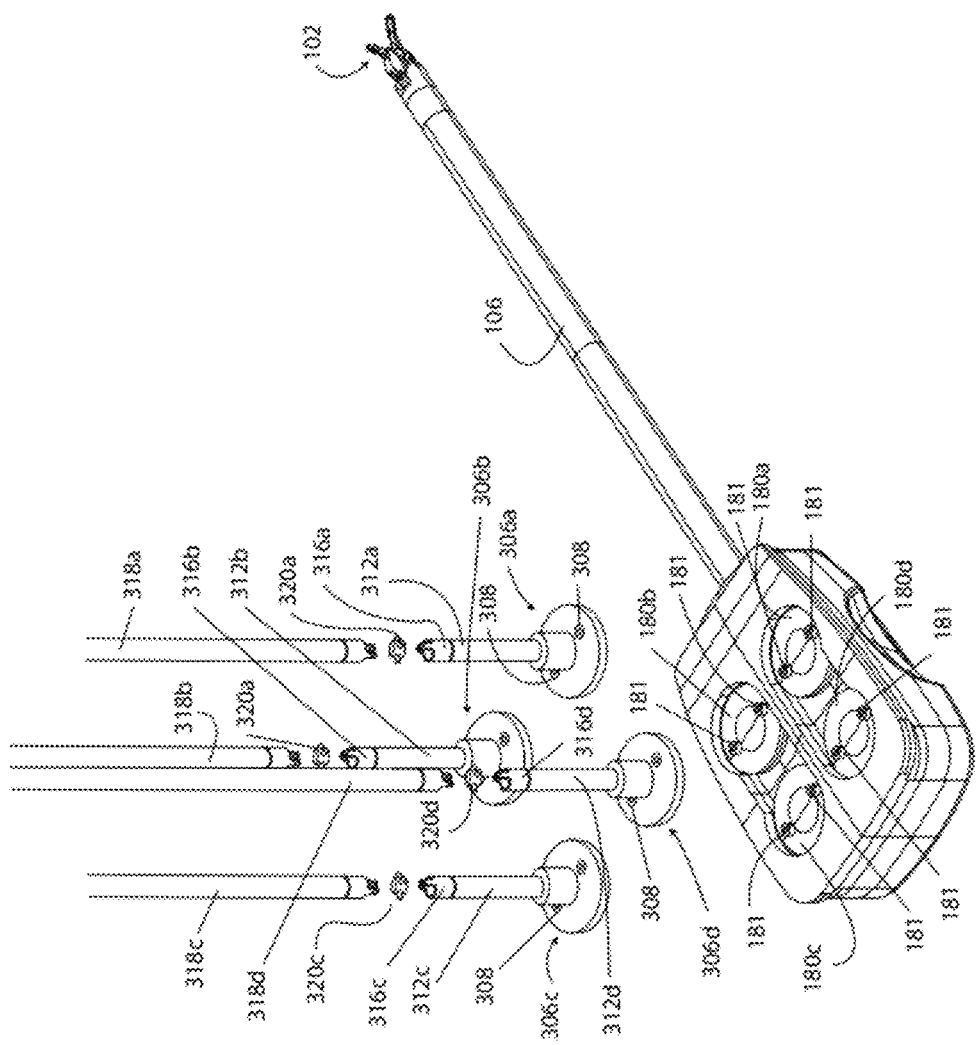
FIG. 9B is an exploded view of a portion of the mechanical linkage assembly of FIG. 9A.

The mechanical linkage assembly 300 is illustrated in more detail in FIGS. 9A-9C, and as with the wrist/arm/pulley system described above, detailed views of the slave assembly 100 are shown. The coupling between the mechanical linkage assembly 300 and the master assembly 200 can be identical to that of the slave assembly 100 and thus need not be shown or described in detail.

As shown in FIG. 9A, the mechanical linkage assembly 300 can generally extend between the master pulley housing 210 and the slave pulley housing 110 and can transfer motion therebetween. In some embodiments, the mechanical linkage assembly 300 can include four drive rods 302a, 302b, 302c, 302d (jointly "302") that correspond with the four pulleys 166, 266 in each of the housings 110, 210. Each drive rod 302 can be coupled to one of the pulleys 266 in the master pulley housing 210 and one of the pulleys 166 in the slave pulley housing 110. In addition, each drive rod 302 can rotate in response to and/or to cause rotation of each of the pulleys 166, 266. In this way, movement is communicated between the master assembly 200 and the slave assembly 100.

While the drive rods 302 can have any configuration suitable for transferring rotational motion, in the illustrated embodiment, each drive rod 302 includes a series of linkages and a coupling mechanism that can provide a secure mating between the linkages and the connector plates 180, 280 of the pulleys 166, 266. For example, as shown in FIG. 9A, the drive rods 302 can include corresponding superior couplers 304a, 304b, 304c, 304d (jointly "304") that connect with the connector plates 280 of the master pulleys 266. The drive rods 302 can also include inferior coupler 306a, 306b, 306c, 306d (jointly "306") that connect with corresponding connector plates 180 of the slave pulleys 166. The couplers 304, 306 can have any size and shape as needed, but in the illustrated embodiment they are substantially disk-shaped members that are of the same size as the connector plates 180, 280. Referring to FIG. 9B which shows the coupling to the slave assembly 100, there are many ways in which to mate the couplers 306 to the connector plates 180. In the illustrated embodiment, the connector plates 180 each have two nubs 181 extending therefrom that are received by the couplers 306 and secured by fasteners 308. This connection ensures that the connector plates 180 and their corresponding couplers 306 rotate at the same rate, and do not rotate relative to one another.

Referring back to FIG. 9A, the coupling mechanism can also include superior receiving members 310a, 310b, 310c, 310d (jointly "310") that can extend perpendicularly from the superior couplers 304, as well as inferior receiving members 312a, 312b, 312c, 312d (jointly "312") that can extend perpendicularly from the inferior couplers 306. Each receiving member 310, 312 can be a tubular member having a diameter less than that of the coupler 306 and that is configured to receive a linkage of the corresponding drive rod 302 therein. In some embodiments, the receiving members 310, 312 can be integrally formed with the superior and inferior couplers 304, 306 and/or can be coupled thereto by any mechanism known in the art such that they are rigidly coupled together and thus incapable of rotation relative to each other.

The superior receiving member 310 can be configured to receive and secure a superior linkage 314a, 314b, 314c, 314d (jointly "314") of a particular drive rod 302 therein. The superior linkages 314 can have an outer diameter less than an inner diameter of the receiving members 310 so that a superior portion of the superior linkages 314 can fit inside the receiving member 310. Likewise, the inferior receiving members 312 can each receive an inferior linkage 316a, 316b, 316c, 316d (jointly, "316") of the corresponding drive rod 302 therein. A bolt or other fastening mechanism can extend laterally through each linkage 314, 316 and its corresponding receiving member 310, 312 to secure the two together and to prevent the linkages 314, 316 from rotating relative to the receiving members 310, 312. The superior and inferior linkages 314, 316 can therefore remain substantially perpendicular to the superior and inferior couplers 304, 306, as well as to the longitudinal axes of the master arm 206 and the slave arm 106.

On an end of the linkages 314, 316 opposite to that held within the receiving members 310, 312, each of the superior and inferior linkages 314, 316 can couple to a middle linkage 318a, 318b, 318c, 318d (jointly "318") of the drive rods 302 such that the middle linkages 318 connect with the superior and inferior linkages 314, 316. The coupling between the middle linkages 318 and the superior and inferior linkages 314, 316 can be any sort of joint known in the art that allows pivoting of the linkages 314, 316, 318 in different directions, but preferably limits pivoting of the linkages 314, 316, 318 to one dimension. This allows the parallel orientation of the master and slave assemblies 200, 100 to be maintained while also allowing the entire drive rod 302 to be rotated as a unit. For example, as shown in FIGS. 9B and 9C, the coupling between the linkages 314, 316, 318 can be universal joints 320a, 320b, 320c, 320d (jointly "320") that allow each of the linkages 314, 316, 318 to pivot in one direction only, while allowing each linkage 314, 316, 318 to pivot in a direction different than the other linkages 314, 316, 318. A universal joint is particularly useful for transferring rotational motion, however any suitable joint can be used. The middle linkages 318 can generally have a length that is substantially greater than a length of the superior and inferior linkages 314, 316, while the superior and inferior linkages 314, 316 can have substantially the same length. As will be appreciated by those of ordinary skill in the art, the linkages 314, 316, 318 can have any length desired. In some embodiments, the superior, inferior, and middle linkages 314, 316, 318 can all have the same diameter, although they can optionally have different diameters if desired.

It is to be appreciated that in general, a 1:1 ratio between movement of the input tool 202 and movement of the end effector 102 is maintained regardless of the depth of penetration of the end effector 102 within a patient because the input tool 202 and the end effector 102 are of substantially equal distance from the pivot plane P. In some embodiments however, the mechanical linkage assembly 300 can include features that allow scaled motion between the input tool 202 and the end effector 102. For example, if the diameters of the pulleys 166, 266 are equal, then the ratio of input to output is 1 to 1. If the diameter of the pulley 266 is double that of the diameter of the pulley 166, then the ratio of the input to output is 2 to 1 such that the size of motion inputted into the system through the master assembly 200 will result in motion scaled by half in the slave assembly 100. A person skilled in the art will appreciate the variations and possibilities of scaled motion between the master assembly 200 and the slave assembly 100.

In use, mimicked movement can be transferred from the input tool 202 to the end effector 102. For example, if the input tool 202 on the master assembly 200 is pivoted or pitched in a first direction relative to the arm 206, the two cables 228a, 228b disposed around the wrist pulleys 224a, 224b are pulled in the first direction. The two cables 228a, 228b extend through the master arm 206 and around the pulley 266a in the master pulley housing 210, and thus cause the pulley 266a to also rotate in the first direction. Since there can be a rigid coupling between the pulley 266a and its drive rod 302a, the drive rod 302a is also rotated in the first direction. There can also be a rigid coupling between the drive rod 302a and the pulley 166a in the slave pulley housing 110. The pulley 166a in the slave pulley housing 110 is therefore rotated, thereby pulling on the two cables 128a, 128b that extend through the slave arm 106 to the corresponding pulleys 124a, 124b in the slave wrist 108. The two cables 128a, 128b rotate each of the two wrist pulleys 124a, 124b in the first direction, thereby causing the end effector 102 to also pivot or pitch in the first direction. In this way, mimicked motion is transferred from the input tool 202 to the end effector 102. Similar mechanics apply to the other three types of movement: rotation of the master arm 206 about its longitudinal axis to rotate the slave arm 206 about its longitudinal axis, and pivoting of each of the jaw members 234, 236 relative to the input tool 202 and the arm 206 to cause pivoting of the jaw members 134, 136 relative to the end effector 202 and the arm 106.

Surgical System Coupling Assembly

Figure 10B:
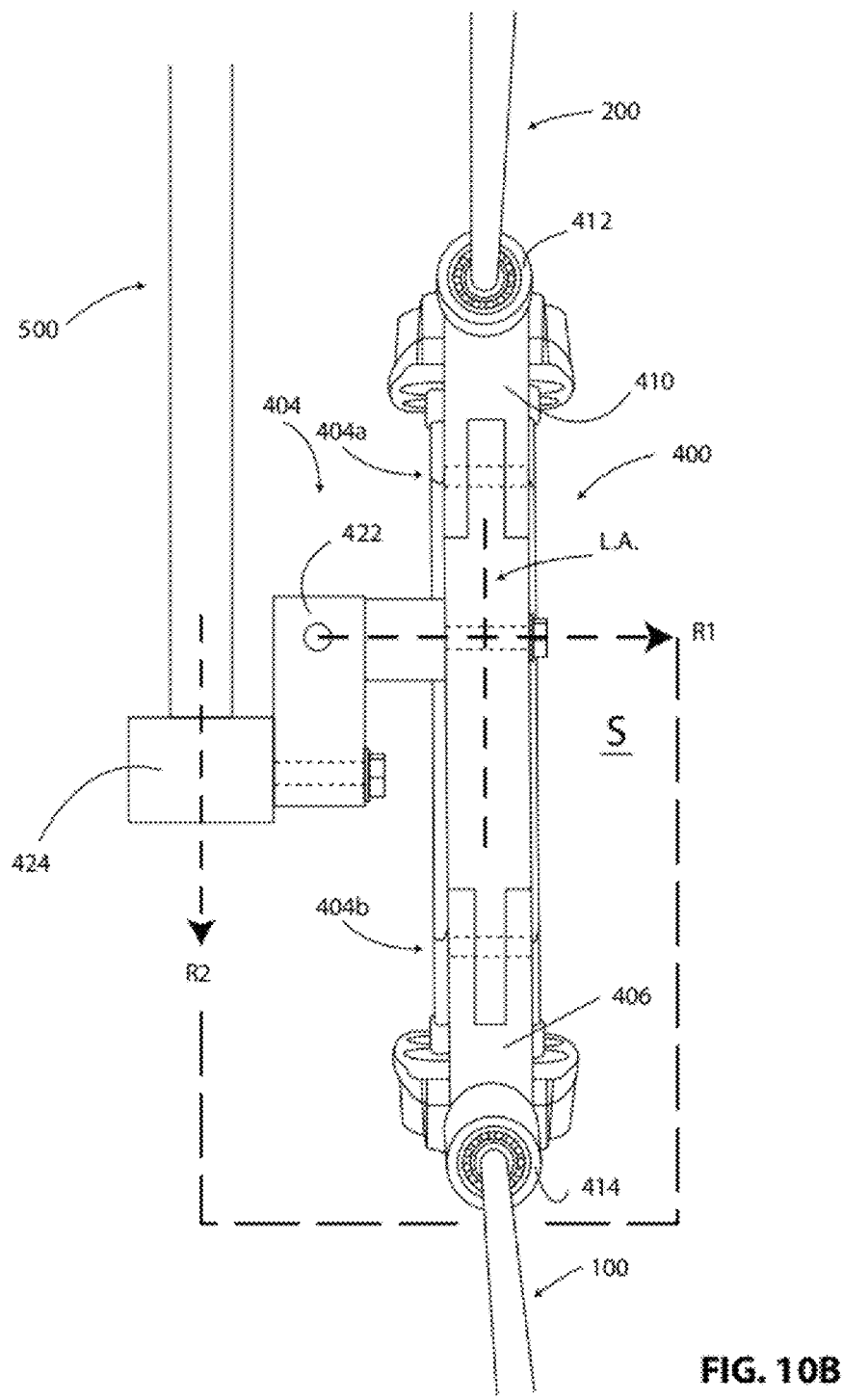
FIG. 10B is a perspective view of a dual-axis swivel joint associated with the coupling assembly of FIG. 10A.

As shown in FIG. 3, the coupling assembly 400 can generally maintain parallel alignment between the master assembly 200 and the slave assembly 100. It can also couple the master and slave assemblies 200, 100 to the floating frame 500. Referring to FIGS. 10A and 10B, the coupling assembly 400 can therefore include a stabilization member 402 that extends between the master and the slave assemblies 200, 100 to maintain their alignment, and a dual-axis swivel joint 404 that can be coupled between the stabilization member 402 and the floating frame 500 to couple the two together.

Figure 10C:
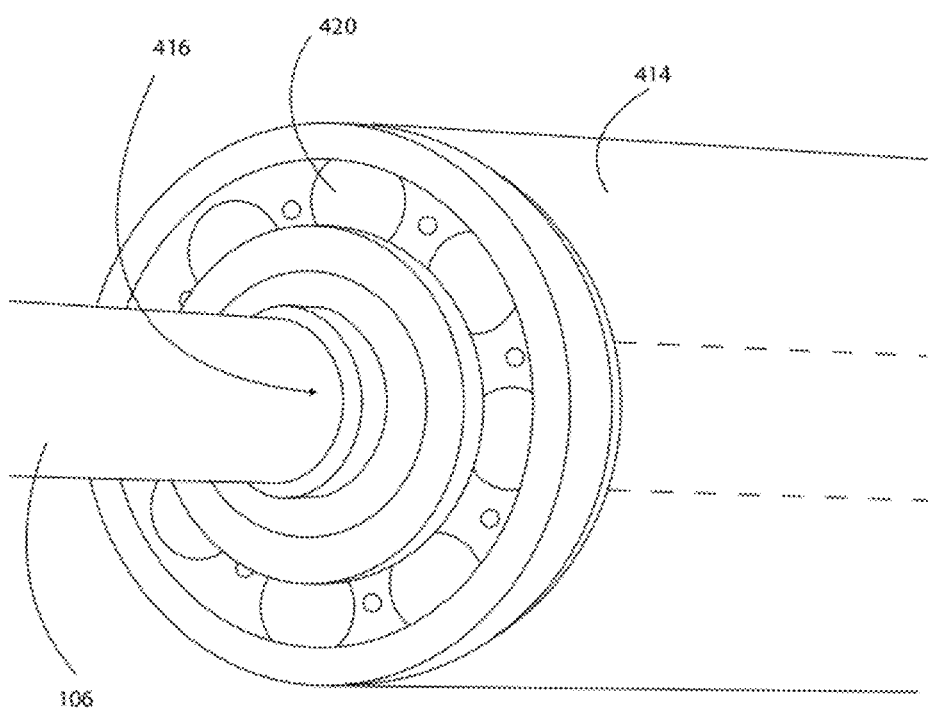
FIG. 10C is a perspective view of a bearing associated with the coupling assembly of FIG. 10A.

While the stabilization member 402 can have many configurations, in the illustrated embodiment, the stabilization member 402 can include three linkages 406, 408, 410 coupled between a master bearing 412 and a slave bearing 414 that receive the master and slave arms 206, 106, respectively. The master and the slave bearings 412, 414 can function to couple the linkages 406, 408, 410 of the stabilization member 402 to the master and the slave arms 206, 106. While the bearings 412, 414 can be positioned anywhere along the master and the slave arms 206, 106, to avoid interference of the stabilization links 406, 408, 410 with tissue during insertion of the slave arm 106 into a body cavity, in the illustrated embodiment they are positioned just forward of the pulley housings 210, 110. The bearings 412, 414 can be, for example, ball bearings, the details of which are shown in more detail in FIG. 10C. Each of the bearings 412, 414 can have an opening 416, 418 formed therethrough with a bearing surface (not shown) and ball bearings 420 disposed therein. The master and the slave arms 206, 106 can extend through each of their respective bearings 412, 414 and can rotate relative to the bearings 412, 414 against the bearing surface. In this way, rotation of the master and the slave arms 206, 106 is not impinged.

The three linkages 406, 408, 410 of the stabilization member 402 can extend between the master bearing 412 and the slave bearing 414. In particular, the superior stabilization linkage 410 can extend substantially perpendicularly from the master bearing 412, and the inferior stabilization linkage 406 can extend substantially perpendicularly from the slave bearing 414. In some embodiments, the superior and inferior stabilization linkages 410, 406 can be integrally and/or unitarily formed with the master and the slave bearings 412, 414, respectively, such that they are rigidly and fixedly disposed relative thereto. In other embodiments, they can be coupled together by any mechanism known in the art, including fixation members, joints, etc. The middle stabilization linkage 408 can connect the superior linkage 410 and the inferior linkage 406. The three linkages 406, 408, 410 can couple together by way of, for example, a clevis style joint and/or hinge style joint, allowing pivoting of the linkages 406, 408, 410 relative to one another in one dimension. For example, the linkage 406 can be coupled to the linkage 408 by a pivot joint 404b, and the linkage 410 can be coupled to the linkage 408 by a pivot joint 404a. This allows the master assembly 200 and the slave assembly 100 to surge slightly relative to one another to maintain their parallel orientation during manipulation of the assembly 10, while fixing all rotational degrees of freedom relative to one another. For example, when the surgical system 10 pitches about a pitch axis of the dual-axis swivel joint 404 as described below, the joints 404a, 404b can remained fixed such that motion of the slave assembly 100 and the master assembly 200 is substantially the same. When the surgical system 10 remains fixed relative to the pitch axis of the dual-axis swivel joint 404, the joints 404a, 404b are free to pivot, thereby allowing a small amount of surging of the master assembly 200 and the slave assembly 100 relative to one another.

The dual-axis swivel joint 404 of the coupling assembly 400 can generally be configured to provide two rotational degrees of freedom to the surgical system 10, namely pitch and yaw. As shown in FIGS. 2 and 10B, the dual-axis swivel joint 404 can be coupled between the middle stabilization member 408 and the floating frame 500. While the swivel joint 404 can couple to any portion of the middle stabilization member 408, in the illustrated embodiment, it is coupled to the member 408 at a location just superior of the midpoint.

The dual-axis swivel joint 404 can have any orientation as desired. In some embodiments, a first swivel joint 422 can be coupled to the middle stabilization member 408 in an orientation such that its central rotational axis R1 is substantially perpendicular to a longitudinal axis L.A. of the middle stabilization member 408. The first swivel joint 422 can allow the surgical system 10 to rotate about the first swivel joint axis R1, i.e., to pitch about the surgical system's pitch axis (illustrated in FIG. 3). A second swivel joint 424 can have a central rotational axis R2 oriented substantially perpendicular to the central axis R1 of the first swivel joint 422 and substantially parallel with the longitudinal axis L.A. of the middle stabilization member 408. The second swivel joint 424 can allow the surgical system 10 to rotate about the second swivel joint axis R2, i.e., to yaw about the surgical system's yaw axis (illustrated in FIG. 3). In this way, the dual-axis swivel joint 404 can provide the surgical system 10 with the two rotational degrees of freedom, i.e., the ability to pitch and to yaw. The third rotational degree of freedom, roll, is not provided by this coupling. Thus the surgical system 10 can be constrained in the third rotational degree of freedom such that the surgical system 10 cannot roll about its roll axis. As will be appreciated by those having skill in the art, a third swivel joint could be used if desired to provide the surgical system 10 with the third rotational degree of freedom.

Figure 4B:
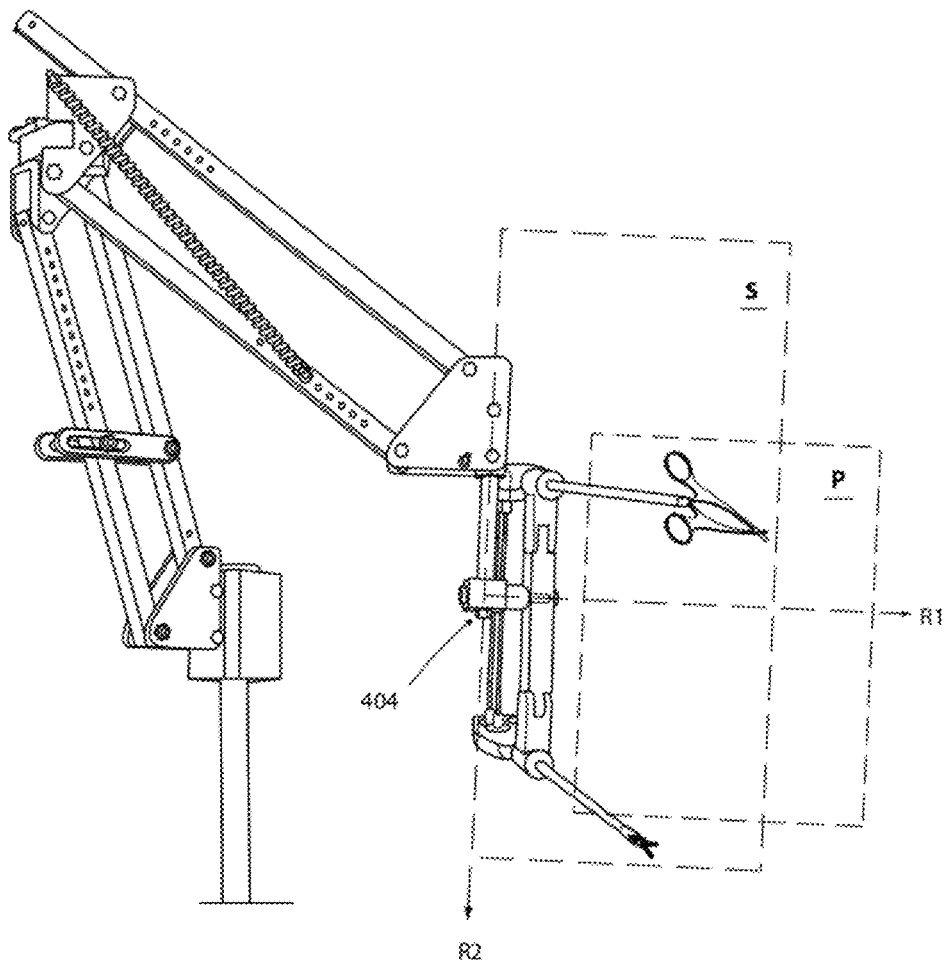
FIG. 4B is a perspective view of the surgical system and an exemplary floating frame of FIG. 2 illustrating an exemplary swivel plane and pivot plane.
Figure 10D:
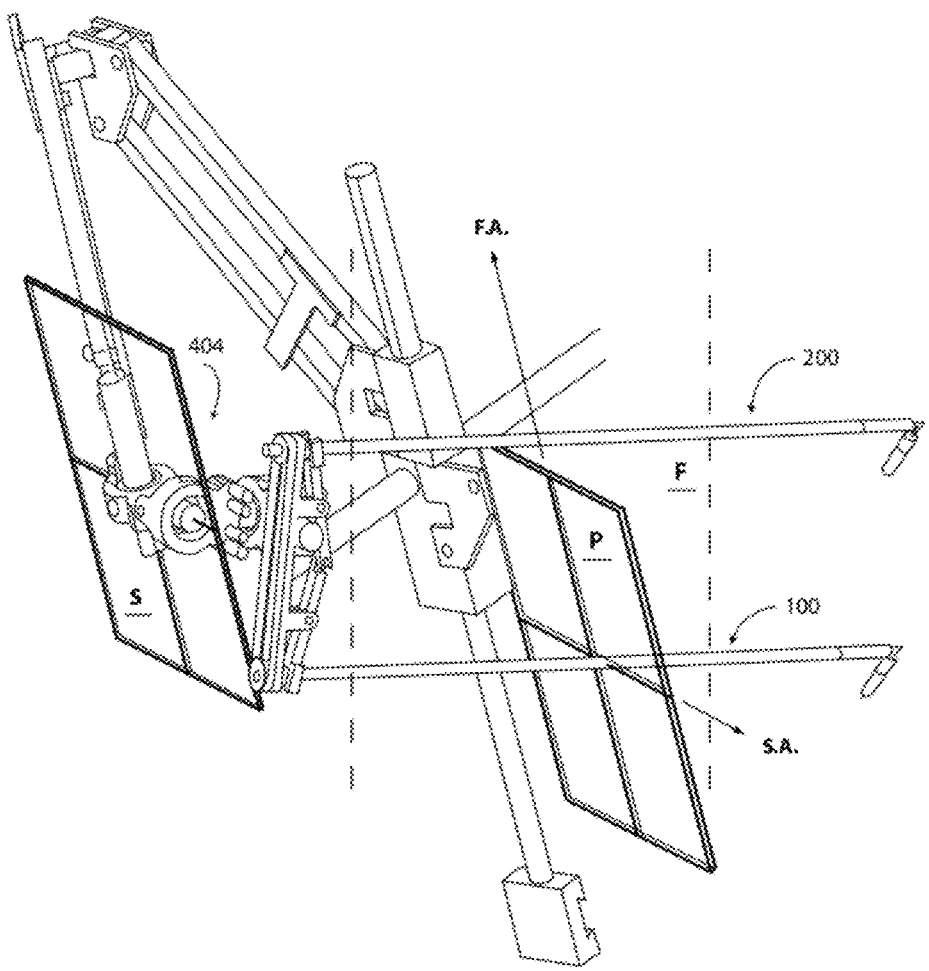
FIG. 10D is a perspective view of the swivel joint of FIG. 10B illustrating an exemplary swivel plane and pivot plane.

In some embodiments, the dual-axis swivel joint 404 can also define the pivot plane P, previously discussed with regard to FIGS. 4A and 4B. The two axes R1 and R2 of the dual-axis swivel joint 404 can define a swivel plane S, as shown in FIGS. 10B and 10D. The pivot plane P can be parallel with the swivel plane S, with the additional requirement that the pivot plane P extend through the surgical access point A when the slave assembly 100 is disposed through an access point A in a tissue surface. Thus, the orientation of the pivot plane P can change with the orientation of the swivel joint 404 as the surgical system 10 is moved so that it remains parallel with the swivel plane S. In an alternative embodiment, the swivel plane S can also be defined by R2 and an axis parallel to R1 that extends through the pivot joint 404*a* and/or the pivot joint 404*b*. Thus, regardless of the orientation of the surgical system 10, the swivel plane S can be defined by any one of the above noted parallel planes defined by the stabilization member 402.

As noted above, the pivot plane P, and thus the swivel plane S, also has a relationship with the first plane F, defined by the longitudinal axes of the slave assembly 100 and the master assembly 200. In particular, the first plane F has a first axis F.A. that is parallel with the first plane F and about which the surgical system 10 can yaw. In addition, the first plane F has a second axis S.A. that is transverse to the first plane F. The first axis F.A. and the second axis S.A. define a plane that is parallel with the pivot plane P and the swivel plane S and/or defines the pivot plane P. In some embodiments, the pivot plane P can be oriented perpendicularly to the first plane F.

The Floating Frame

Figure 11A:
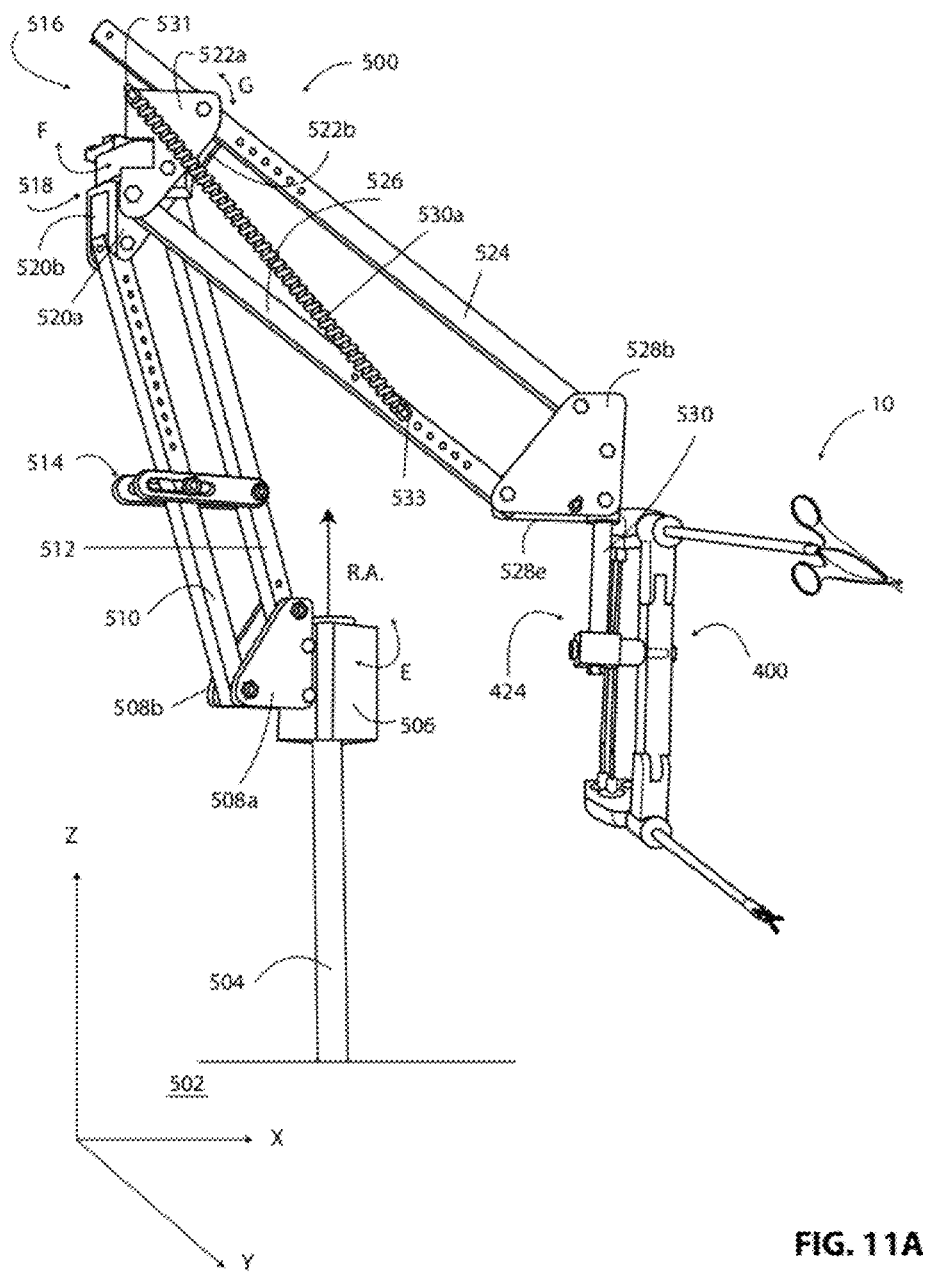
FIG. 11A is a perspective view of the floating frame of FIG. 2.
Figure 11B:
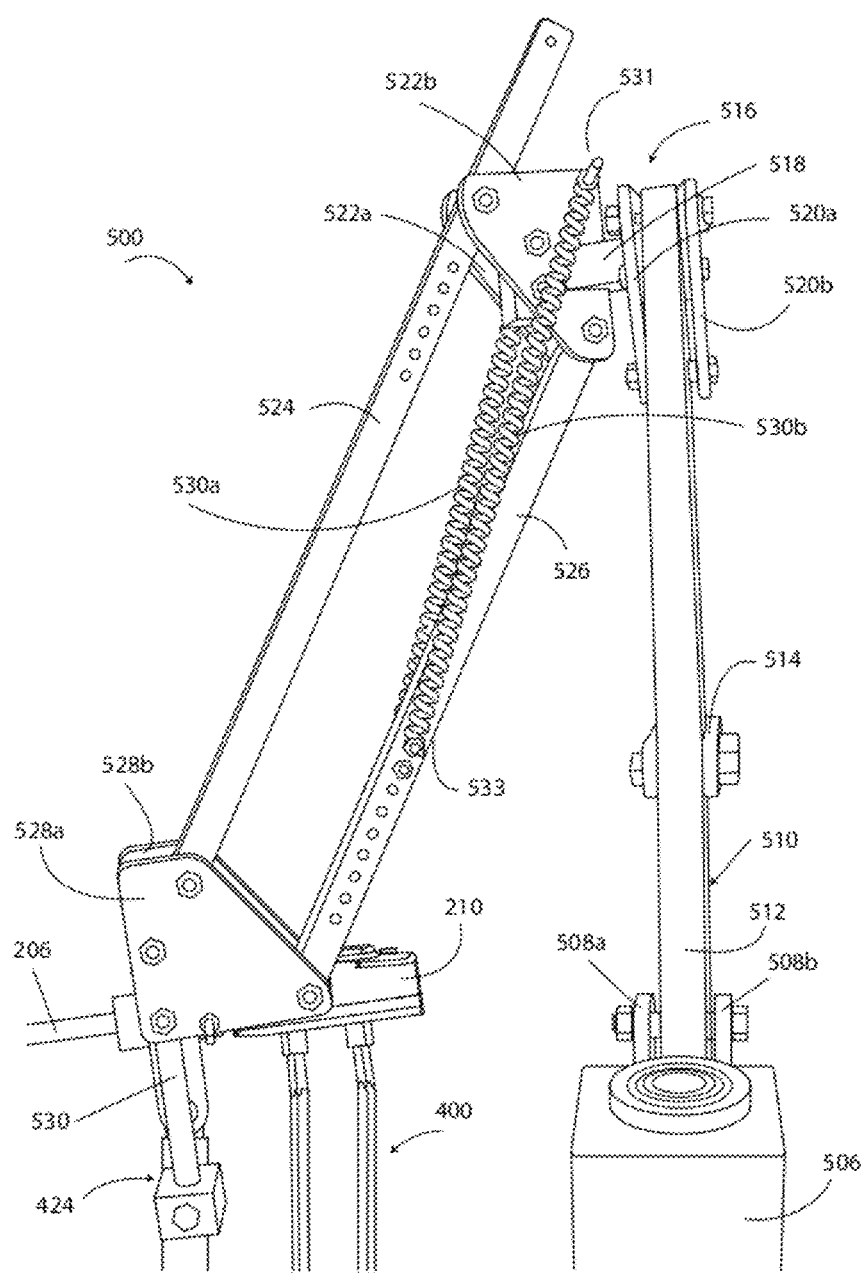
FIG. 11B is a perspective view of a portion of the floating frame of FIG. 11A.

In some embodiments, the floating frame 500 can be used with the surgical system 10, as shown in FIGS. 11A and 11B. The floating frame 500 can generally provide a counterbalance mechanism against the weight of the surgical system 10 so that the surgical system 10 "floats" above a surface and/or a patient and is therefore easy to move. In addition, the floating frame 500 can provide the surgical system 10 with full translational movement along all three coordinate axes such that the system 10 can heave, sway, and surge regardless of its rotational orientation. In addition, the floating frame 500 can be fixed rotationally such that only the dual-axis swivel joint 404 discussed above controls rotational motion of the surgical system 10.

In general, the floating frame 500 can be composed of various rods, brackets, and joints that extend between the dual-axis swivel joint 404 and a fixed and/or stationary base 502 such as a hospital bed, floor, ceiling, operating table, etc. The particular floating frame 500 described herein is only one embodiment, and the configuration and order of the various rods, brackets, and joints is exemplary in nature only. Any frame capable of providing a counterbalance and three dimensional translational movement for the surgical system 10 can be used. Further, any counterbalance system known in the art can be used to balance the weight of the surgical system 10.

As shown in FIGS. 11A and 11B, the floating frame can have a stationary rod 504 that couples to a stationary base 502 such as the hospital bed, floor, ceiling, operating table, etc. The stationary rod 504 can be generally oriented perpendicularly to the floor or other horizontal surface and can be rigidly coupled to the stationary base 502 using typical methods known in the art including clamps, brackets, fasteners, etc. All movement of the floating frame 500 and the surgical system 10 can be relative to the stationary rod 504. A cylindrical bearing 506 can be disposed on the stationary rod 504 to provide the floating frame 500 with 360 degrees of rotation about a central axis R.A. of the stationary rod 504, as shown by arrow E in FIG. 11A. A pair of triangular brackets 508*a*, 508*b* can couple to the cylindrical bearing 506, and two substantially rigid beams or rods 510, 512 can extend upward from the triangular brackets 508*a*, 508*b* away from the stationary rod 504 and substantially in parallel with each other. The brackets 508*a*, 508*b*, rods 510, 512 and cylindrical bearing 506 can be coupled together using any fastening mechanism known in the art including bolts, screws, adhesives, welding, etc. A lateral slide bracket 514 can couple the two rods 510, 512 together and provide a mechanism to adjust the lateral distance between the rods 510, 512.

The two rods 510, 512 can couple into a pivotable joint mechanism 516 that includes two sets of triangular brackets 520*a*, 520*b*, 522*a*, 522*b* joined together by a dual rotation joint 518. The dual rotation joint 518 allows the second set of brackets 522*a*, 522*b*, as well as everything coupled to the brackets 522*a*, 522*b*, to rotate about the z-axis, as shown by arrow F in FIG. 11A. The dual rotation joint 518 also allows the first set of brackets 520*a*, 520*b*, as well as everything coupled to the brackets 520*a*, 520*b*, to rotate about the y-axis, as indicated by arrow G in FIG. 11A. Two substantially rigid rods 524, 526 extend downward from the brackets 522*a*, 522*b* in a substantially parallel orientation and terminate in a pair of brackets 528*a*, 528*b*. A connector rod 530 extends vertically downward from the brackets 528*a*, 528*b* and into the second swivel joint 424 of the dual-axis swivel joint 404 described above. The rods 524, 526, brackets 520*a*, 520*b*, 522*a*, 522*b*, and dual rotation joint 518 can be coupled together using any fastening mechanism known in the art including bolts, screws, adhesives, welding, etc. The movement provided by the floating frame 500 will be described in detail below.

In the illustrated embodiment, the counterbalance for the surgical system 10 can be two coil springs 530*a*, 530*b* coupled to the floating frame 500. The two coil springs 530*a*, 530*b* can couple on one end 531 to the vertical most brackets 522*a*, 522*b* of the floating frame 500 by way of, for example, a hook and fastener connection, and can couple on an opposite end 533 to a mid-portion of the rods 524, 526. Since the rods 524, 526 support the weight of the surgical system 10 through the dual-axis swivel joint 404 and the brackets 528*a*, 528*b*, the springs 530*a*, 530*b* essentially "hold up" the weight of the surgical system 10. The position at which the springs 530*a*, 530*b* couple to the rods 524, 526 can be adjusted to provide the proper balance to the surgical system 10 such that the surgical system 10 is suspended and/or floats in the air. The springs 530*a*, 530*b* can provide a weightless feel to movement of the surgical system 10. As will be appreciated by those having ordinary skill in the art, any counterbalance known in the art can be used to balance the surgical system 10. For example, a hanging weight can be used and/or another type of spring system can be used.

Use

There are many methods for using the above described surgical system 10 and the floating frame 500, and any method steps discussed herein need not be performed in a particular order. In use, the floating frame 500 can provide the surgical system 10 with three translational degrees of freedom. Thus, in positioning the surgical system 10 in preparation for use in a surgical procedure, for example, the surgical system 10 can heave, surge, and sway to be moved into position. In addition, the dual-axis swivel joint 404 provides the surgical system 10 with two rotational degrees of freedom as described above. The surgical system 10 can thus also pitch and yaw as it is moved into position. As noted above, in this embodiment the system 10 is limited from moving with the sixth degree of freedom, or third rotational degree of freedom, i.e., rolling. In this way, and using the five degrees of freedom, the surgical system 10 can be moved into position near a patient.

When the surgical system 10 is in position near a patient, as shown in FIG. 4, the slave arm 106, wrist 108, and end effector 102 can be inserted through a surgical access point A in a tissue surface, such as a trocar T or other access cannula, so that the end effector 102 is disposed within a body cavity. Once the slave arm 106 is disposed through the access point A, the input tool 202 and the end effector 102 are positioned on the same side of the pivot plane P that extends perpendicularly to the longitudinal axis L.S. of the slave assembly 106 and through the access point A. Movement of the master assembly 200 can thus result in mimicked movement of the slave assembly 100 to cause pivoting and surging of the slave assembly 100 about the access point A as needed to perform surgery.

While disposed through the access point A, the slave assembly 100, and thus the surgical assembly 10, is constrained. In particular, the surgical assembly 10 can no longer heave or sway due its confinement in the trocar T, thus removing two of the translational degrees of freedom. However, the surgical system 10 can still surge, pitch, and yaw while constrained by the access point A and thus it, as well as the end effector 102, can have three degrees of freedom.

To perform a surgical procedure, the input tool 202 can be used to control the end effector 102 within the body cavity. For example, the input tool 202 and master arm 206 can be rotated around the longitudinal axis L.M. of the master arm 206 to cause corresponding rotation of the slave arm 106 and end effector 102 about the longitudinal axis L.S. of the slave arm 106. This roll of the end effector 102 is an additional, fourth degree of freedom for the end effector 102. The input tool 202 can also be pivoted or pitched relative to the master arm 206 to cause corresponding pitching of the end effector 102, resulting in an additional, fifth degree of freedom for the end effector 102. However, this degree of freedom is redundant with the pitching of the surgical system 10 provided by the dual-axis swivel joint 404, and thus the end effector has four independent degrees of freedom.

In some embodiments, each of the jaws 234, 236 of the input tool 202 can be opened and closed resulting in corresponding opening and closing of each of the jaw members 134, 136 of the end effector 102. This results in a yawing motion of the jaws 134, 136 relative to the end effector 102, giving the jaws 134, 136 a sixth degree of freedom when added to the pitch provided by the end effector 102. However, this degree of freedom is redundant with the yawing of the surgical system 10 provided by the dual-axis swivel joint 404, and thus the jaws 134, 136 also have four independent degrees of freedom.

A surgical procedure can be performed using these various types of motion available to the end effector 102 and the jaws 134, 136. Once the procedure is complete, the end effector 102, slave wrist 108, and slave arm 106 can be withdrawn from the surgical access point A. A person skilled in the art will appreciate that the above described embodiment has applications in conventional endoscopic and open surgical instrumentation as well application in robotic-assisted surgery.

Surgical System II

Figure 12B:
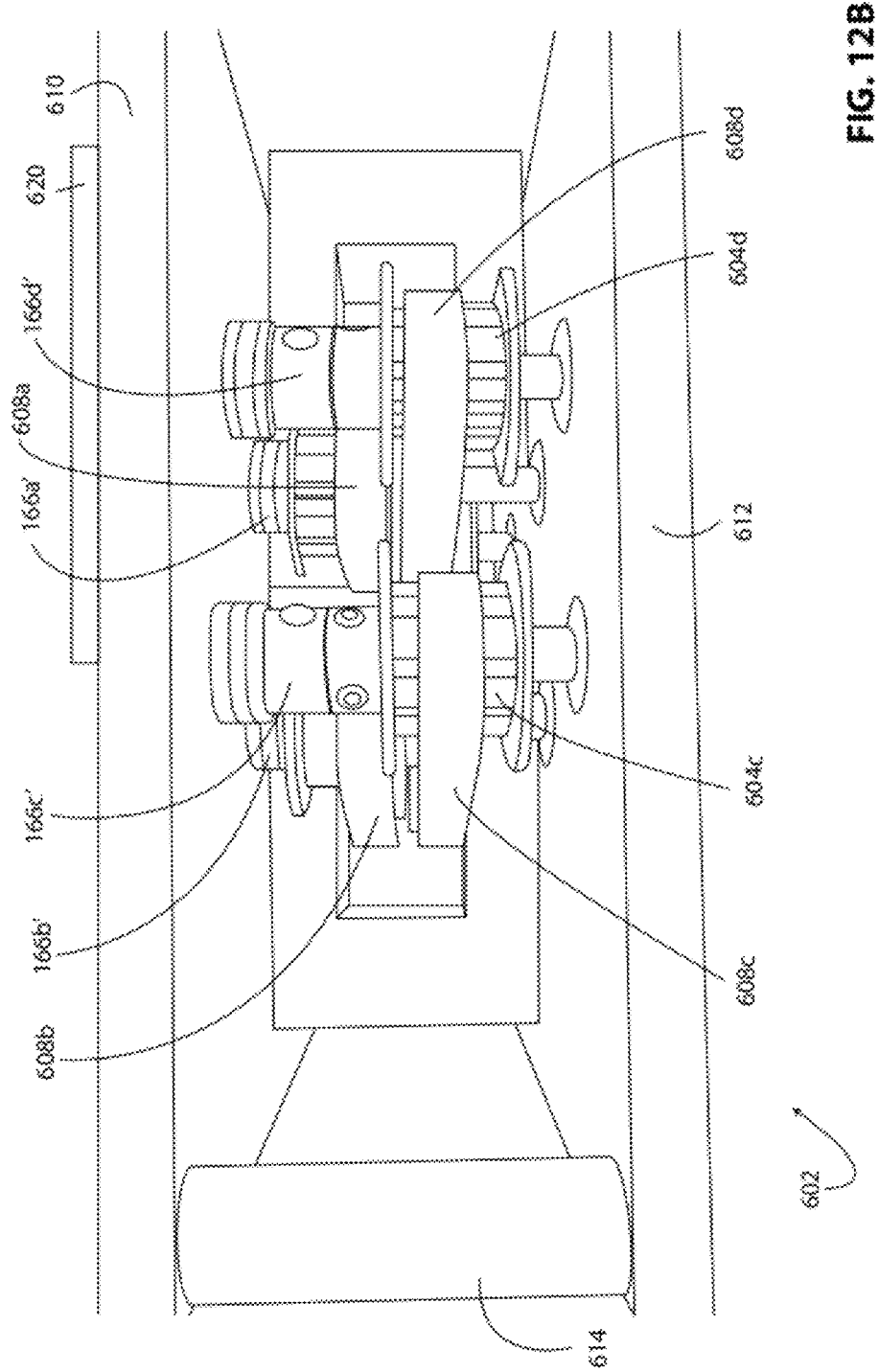
FIG. 12B is a side view of an exemplary housing of the surgical system of FIG. 12A showing exemplary slave pulleys and cables.
Figure 12C:
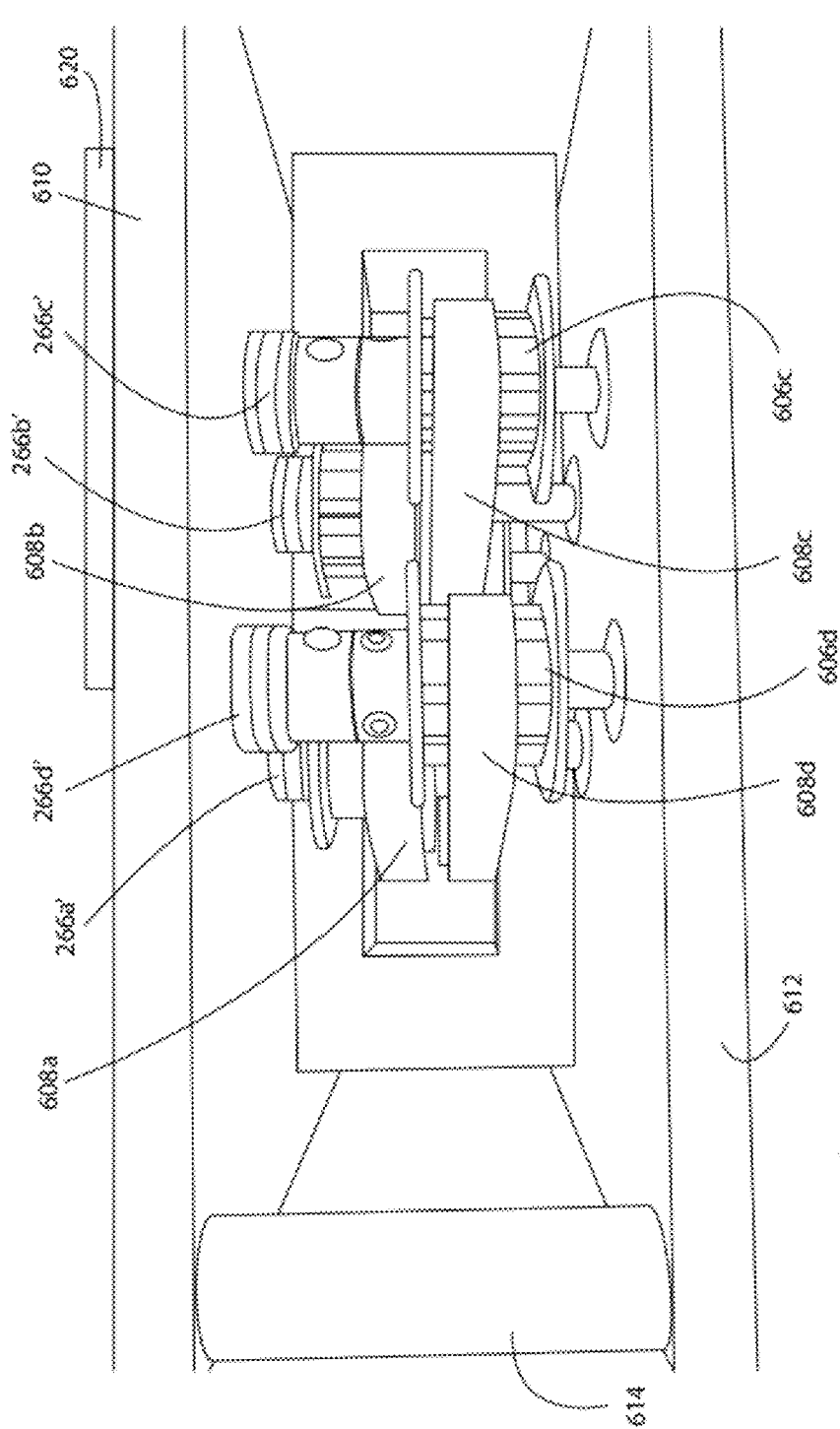
FIG. 12C is an opposite side view of the exemplary housing of FIG. 12B showing exemplary master pulleys.

Another embodiment of a surgical system 600 is illustrated in FIGS. 12A-12C. The surgical system 600 can include identical master and slave assemblies to the embodiment described above, and thus the details thereof will not be repeated. The components of the master and the slave assemblies will be referred to with the same reference numbers as with the surgical system 10, but with primes. The surgical system 600 can optionally couple to the floating frame 500 through the dual-axis swivel joint 404 as described above, and thus the floating frame 500 and dual-axis swivel joint 404 will also not be detailed again. It is to be noted, however, that because the surgical system 600 does not include a stabilization member 404 that allows its master and slave assemblies 200', 100' to surge slightly relative to one another, mimicked motion of the master and slave assemblies is generally only useful for relatively small angles of pitching and/or yawing.

FIG. 12A illustrates the surgical assembly 600, while FIG. 12B illustrates the slave side of the surgical system 600 and FIG. 12C illustrates the master side of the surgical system 600. In this embodiment, the pulley housings 210', 110' of the master and the slave assemblies 200', 100' are coupled rigidly together within a housing 602. A bracket 620 extends between the master and slave housings 210', 110' to secure them to the housing 602. The housing 602 can contain the pulley systems disposed within each of the pulley housings 210', 110' as described above. However the mechanical linkage assembly described above is replaced with connector pulleys that transfer movement of the master assembly 200' to the slave assembly 100'. In particular, each of the slave pulleys 166a', 166b', 166c', 166d' (jointly "166'") within the slave housing 110' can be extended within the housing 602 as shown in FIG. 12B to have corresponding slave connector pulleys 604a, 604b, 604c, 604d (jointly "604"). Each of the master pulleys 266a', 266b', 266c', 266d' (jointly "266") can also be extended to have corresponding slave connector pulleys 606a, 606b, 606c, 606d (jointly "606") similar to the master connector pulleys 604.

Each master connector pulley 606 and its corresponding slave connector pulley 604 can be connected by a band 608a, 608b, 608c, 608d (jointly "608") that transfers rotation between the two connector pulleys 604, 606. Thus, for example, as the input tool 202' is pitched relative to the master arm 206', the corresponding master pulley 266a' within the housing 602 rotates, causing rotation of its connector pulley 606a. Since the master connector pulley 606a is connected by the band 608a to the slave connector pulley 606a, the slave connector pulley 606a rotates to cause corresponding rotation of the slave pulley 166a', which in turn causes the end effector 102' to pitch relative to the slave arm 106'. The same applies to all movement of the input tool 202' and rotation thereof.

The housing 602 can take any suitable form in the art, but in the illustrated embodiment, it has an open construction composed of two planar portions 610, 612 connected by four rivets or fasteners 614 at the corners. In addition, the pulleys 166', 266' and the connector pulleys 604, 606 can be coupled together by any mechanism known in the art, including rotary fasteners, adhesives, welding, press fit, etc. The movement available to the surgical system 600 is the same as for the system 10. When unconstrained by a trocar T, the surgical system 600 can have five degrees of freedom. When constrained within a trocar T, the surgical system 600 has three degrees of freedom and the end effector 102' has four independent degrees of freedom.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. By way of non-limiting example, the scraper and/or sorbent can be removed, cleaned, re-coated with a hydrophilic material, sterilized, and reused. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A minimally invasive surgical system, comprising:
an elongate master assembly defining a longitudinal axis and having a tool coupled to a forward end thereof and a master pulley housing at a rearward end thereof;
an elongate slave assembly defining a longitudinal axis and having an end effector coupled to a forward end thereof and a slave pulley housing at a rearward end thereof, the longitudinal axis of the elongate master assembly and the longitudinal axis of the elongate slave assembly defining a first plane extending therethrough;
a mechanical coupling system extending between the rearward ends of the master assembly and the slave assembly and being configured to transfer corresponding motion of the tool to the end effector such that the end effector mimics motion of the tool; and
a stabilization member coupled between the master assembly and the slave assembly and configured to maintain the master assembly and the slave assembly in a substantially parallel orientation while allowing the master and slave assemblies to move towards and away from one another,
wherein the first plane defines a first axis parallel to the first plane about which the master and slave assemblies yaw and a second axis transverse to the first plane, the first axis and the second axis defining a pivot plane transverse to the first plane;
wherein, when a forward portion of the slave assembly is inserted into a body cavity through an access point in a tissue surface, the pivot plane extends through the access point and the tool and the end effector are positioned forward of the pivot plane;
wherein the mechanical coupling system comprises a plurality of rotatable drive rods, each of the drive rods having a first end coupled to a pulley in the master pulley housing and a second end coupled to a pulley in the slave pulley housing.

2. The surgical system of claim 1, wherein, when the forward portion of the slave assembly is inserted into a body cavity through an access point in a tissue surface, the mechanical coupling system is positioned rearward of the pivot plane.

3. The surgical system of claim 1, wherein the pivot plane is perpendicular to the first plane.

4. The surgical system of claim 1, further comprising a floating frame coupled to the stabilization member and configured to allow simultaneous movement of the master assembly and the slave assembly together in parallel with three translational degrees of freedom that include surging, heaving, and swaying while being rotationally fixed.

5. The surgical system of claim 4, wherein the floating frame is coupled to the stabilization member through a dual-axis swivel joint that is configured to allow simultaneous movement of the master assembly and the slave assembly together in parallel with two rotational degrees of freedom that include pitching and yawing, the third rolling rotational degree of freedom being fixed.

6. The surgical system of claim 1, wherein the mechanical coupling system is configured to transfer rotation of the tool about a longitudinal axis of the master assembly to the end effector to effect mimicked rotation of the end effector about a longitudinal axis of the slave assembly.

7. The surgical system of claim 1, wherein the mechanical coupling system is configured to transfer pivoting of the tool relative to the master assembly to the end effector to effect mimicked pivoting of the end effector relative to the slave assembly.

8. The surgical system of claim 1, wherein the mechanical coupling system is configured to transfer opening and closing of the tool to the end effector to effect mimicked opening and closing of the end effector.

9. The surgical system of claim 1, wherein the mechanical coupling system includes a first linkage assembly being configured to transfer to the end effector rotation of the tool relative to the longitudinal axis of the master assembly, a second linkage assembly being configured to transfer to the end effector pivoting of the tool relative to the master assembly, a third linkage assembly being configured to transfer to the end effector pivoting of a first handle of the tool, and a fourth linkage assembly being configured to transfer to the end effector pivoting of a second handle of the tool, to thereby effect mimicked motion of the end effector.

10. The surgical system of claim 1, wherein the mechanical coupling system is configured to scale motion of the tool and transfer the scaled motion to the end effector.

11. The surgical system of claim 1, wherein a length of the elongate master assembly is substantially the same as a length of the elongate slave assembly.

* * * * *